(12) United States Patent
Constantz et al.

(10) Patent No.: US 7,815,596 B2
(45) Date of Patent: Oct. 19, 2010

(54) LOCALIZED FLUID DELIVERY HAVING A POROUS APPLICATOR AND METHODS FOR USING THE SAME

(75) Inventors: Brent R. Constantz, Menlo Park, CA (US); Jerome B. Riebman, Sunnyvale, CA (US); Philip R Houle, Menlo Park, CA (US)

(73) Assignee: Cordis Corporation, Bridgewater, NJ (US)

( * ) Notice: Subject to any disclaimer, the term of this patent is extended or adjusted under 35 U.S.C. 154(b) by 1464 days.

(21) Appl. No.: 10/087,599

(22) Filed: Feb. 28, 2002

(65) Prior Publication Data

US 2003/0163081 A1 Aug. 28, 2003

(51) Int. Cl.
*A61M 1/00* (2006.01)
(52) U.S. Cl. .......................... 604/35; 604/506; 604/508
(58) Field of Classification Search ................. 604/113, 604/500, 20–22, 506–508, 93.01, 264, 35, 604/115, 26
See application file for complete search history.

(56) References Cited

U.S. PATENT DOCUMENTS

| | | | |
|---|---|---|---|
| 4,264,018 A * | 4/1981 | Warren | 222/95 |
| 4,344,434 A * | 8/1982 | Robertson | 604/334 |
| 4,445,892 A | 5/1984 | Hussein et al. | |
| 4,573,966 A | 3/1986 | Weikl et al. | |
| 4,589,868 A * | 5/1986 | Dretler | 604/96.01 |
| 4,610,662 A | 9/1986 | Weikl et al. | |
| 4,636,195 A | 1/1987 | Wolinsky | |
| 4,655,746 A | 4/1987 | Daniels et al. | |
| 4,690,672 A | 9/1987 | Veltrup | |
| 4,717,387 A | 1/1988 | Inoue | |
| 4,810,246 A * | 3/1989 | Frisch et al. | 604/175 |
| 4,824,436 A | 4/1989 | Wolinsky | |
| 4,911,163 A | 3/1990 | Fina | |
| 4,959,054 A * | 9/1990 | Heimke et al. | 604/175 |
| 4,976,733 A | 12/1990 | Girardot | |
| 5,059,178 A | 10/1991 | Ya | |
| 5,090,960 A | 2/1992 | Don Michael | |
| 5,167,628 A * | 12/1992 | Boyles | 604/103.07 |
| 5,195,955 A | 3/1993 | Don Michael | |
| 5,222,941 A | 6/1993 | Don Michael | |
| 5,242,428 A * | 9/1993 | Palestrant | 604/265 |

(Continued)

FOREIGN PATENT DOCUMENTS

WO 94/05361 A1 3/1994

(Continued)

OTHER PUBLICATIONS

International Search Report mailed Oct. 6, 2003 for corresponding Application No. PCT/US03/05725.

(Continued)

*Primary Examiner*—Nicholas D Lucchesi
*Assistant Examiner*—Quynh-Nhu H Vu

(57) ABSTRACT

Fluid delivery devices having a porous applicator, as well as methods for using the same in the highly localized delivery of fluid to a target site, are provided. The subject devices have a porous applicator through which fluid must flow in order to contact the target delivery site. The subject devices find use in a variety of fluid delivery applications in which the localized delivery of a fluid to a target site is desired. Also provided are systems and kits that include the subject fluid delivery devices.

1 Claim, 15 Drawing Sheets

U.S. PATENT DOCUMENTS

| | | | |
|---|---|---|---|
| 5,279,565 A | | 1/1994 | Klein |
| 5,370,608 A * | | 12/1994 | Sahota et al. .................. 604/20 |
| 5,370,609 A | | 12/1994 | Drasler et al. |
| 5,380,284 A | | 1/1995 | Don Michael |
| 5,407,423 A * | | 4/1995 | Yoon ............................. 604/1 |
| 5,443,446 A | | 8/1995 | Shturman |
| 5,451,204 A | | 9/1995 | Yoon |
| 5,462,529 A * | | 10/1995 | Simpson et al. ......... 604/101.04 |
| 5,496,267 A | | 3/1996 | Drasler et al. |
| 5,695,460 A | | 12/1997 | Siegel |
| 5,758,675 A | | 6/1998 | Scheyer |
| 5,785,675 A | | 7/1998 | Drasler et al. |
| 5,833,650 A | | 11/1998 | Imran |
| 5,842,971 A * | | 12/1998 | Yoon ........................... 600/101 |
| 5,913,854 A | | 6/1999 | Maguire et al. |
| 5,913,856 A * | | 6/1999 | Chia et al. ..................... 606/41 |
| 5,916,193 A * | | 6/1999 | Stevens et al. .............. 604/509 |
| 5,985,307 A * | | 11/1999 | Hanson et al. ............... 424/423 |
| 5,997,497 A * | | 12/1999 | Nita et al. ..................... 604/22 |
| 6,033,390 A * | | 3/2000 | von Dyck .................... 604/332 |
| 6,047,700 A | | 4/2000 | Eggers |
| 6,083,573 A | | 7/2000 | Tarumi |
| 6,093,180 A | | 7/2000 | Elsberry |
| 6,113,570 A | | 9/2000 | Siegel |
| 6,139,571 A * | | 10/2000 | Fuller et al. .................. 604/500 |
| 6,156,350 A | | 12/2000 | Constantz |
| 6,190,357 B1 | | 2/2001 | Ferrari |
| 6,228,046 B1 * | | 5/2001 | Brisken ........................ 604/22 |
| 6,270,484 B1 * | | 8/2001 | Yoon ........................... 604/264 |
| 6,290,689 B1 | | 9/2001 | Delaney |
| 6,308,714 B1 | | 10/2001 | Peterson |
| 6,379,345 B1 | | 4/2002 | Constantz |
| 6,387,071 B1 | | 5/2002 | Constantz |
| 6,394,096 B1 | | 5/2002 | Constantz |
| 6,488,671 B1 * | | 12/2002 | Constantz et al. ........... 604/500 |
| 6,527,979 B2 | | 3/2003 | Constantz |
| 6,533,767 B2 | | 3/2003 | Johansson |
| 6,540,733 B2 | | 4/2003 | Constantz |
| 6,562,020 B1 | | 5/2003 | Constantz |
| 6,602,218 B2 | | 8/2003 | Yoon |
| 6,706,013 B1 * | | 3/2004 | Bhat et al. ................ 604/96.01 |
| 6,755,811 B1 | | 6/2004 | Constantz |
| 6,949,088 B2 * | | 9/2005 | Macrae ....................... 604/275 |
| 6,951,555 B1 * | | 10/2005 | Suresh et al. ................ 604/524 |
| 6,979,293 B2 * | | 12/2005 | Hansmann et al. .......... 600/439 |
| 2001/0031943 A1 * | | 10/2001 | Urie ............................ 604/43 |
| 2003/0009132 A1 * | | 1/2003 | Schwartz et al. ............. 604/152 |
| 2003/0163081 A1 | | 8/2003 | Constantz et al. |
| 2003/0202838 A1 | | 10/2003 | Sun et al. |
| 2006/0184094 A1 * | | 8/2006 | Constantz et al. ............. 604/22 |

FOREIGN PATENT DOCUMENTS

| | | |
|---|---|---|
| WO | WO00/03651 | 1/2000 |
| WO | WO01/05210 | 1/2001 |
| WO | WO01/13985 | 3/2001 |
| WO | WO01/15767 | 3/2001 |
| WO | 02/08082 A1 | 1/2002 |

OTHER PUBLICATIONS

U.S. Appl. No. 09/648,282, filed Sep. 29, 2006, Brent R. Constantz, et al., (Abandoned).

International Search Report mailed Oct. 6, 2003 for corresponding Application No. PCT/US03/05725.

International Search Report mailed Mar. 5, 2010 for corresponding Application No. EP 03 70 9333.

* cited by examiner

LOCALIZED FLUID DELIVERY HAVING A POROUS APPLICATOR AND METHODS FOR USING THE SAME

TECHNICAL FIELD

The field of this invention fluid delivery, particularly localized fluid delivery to a physiological site.

BACKGROUND OF THE INVENTION

There are many medical procedures currently practiced in which a fluid is administered to the subject being treated, where such procedures include drug delivery, imaging agent delivery, irrigation, etc. In many situations, it is desirable to provide for localized fluid delivery to a specific region or location (i.e., site) of the subject being treated. Such situations include those in which a toxic agent is being administered and it is desired to reduce the systemic toxicity of the agent; those in which an expensive agent is being administered and targeted delivery is sufficient for the intended purpose; and the like.

A number of different localized fluid delivery devices have been developed for use in a variety of procedures. For example, numerous and diverse fluid delivery devices, e.g., catheter and non-catheter devices, that provide for localized fluid delivery to a particular site have been developed to be used in a variety of different applications. In many such embodiments, the fluid delivery devices are relatively complex in that they include various isolation elements for producing an isolated environment around the target site. While such devices can be effective, the isolated environment is typically much larger than the target site, resulting in contact of the fluid with unwanted areas adjacent to the target site.

As such, there is a continued need for the development of additional fluid delivery devices for use in localized fluid delivery to a specific region, location or site of a subject. Of particular interest would be the development of such a device that was simple and provided for precise, highly localized delivery of fluid to a target site with minimal, if any, fluid contact to regions adjacent to the target site.

Relevant Literature

U.S. Patents of general interest include: U.S. Pat. Nos. 4,445,892; 4,573,966; 4,610,662; 4,636,195; 4,655,746; 4,690,672; 4,824,436; 4,911,163; 4,976,733; 5,059,178; 5,090,960; 5,167,628; 5,195,955; 5,222,941; 5,370,609; 5,380,284; 5,443,446; 5,462,529; 5,496,267; 5,785,675; and 5,833,650. Also of interest are U.S. Pat. Nos. 5,913,856 and 5,913,854. See also PCT publication No. WO 01/05210. Also of interest are: WO 00/03651; WO 01/13985; and WO 01/15767 and U.S. Pat. No. 6,156,350.

SUMMARY OF THE INVENTION

Fluid delivery devices having a porous applicator, as well as methods for using the same in the highly localized delivery of fluid to a target site, are provided. The subject devices have a porous applicator through which fluid must flow in order to contact the target delivery site. Both open-field surgical, e.g., "hand-held," and percutaneous devices, e.g., for use in intervential approaches, such as beating heart applications, are provided. The subject devices find use in a variety of fluid delivery applications in which the localized delivery of a fluid to a target site is desired. Also provided are systems and kits that include the subject fluid delivery devices.

DESCRIPTION OF THE SPECIFIC EMBODIMENTS

Figure 1A:
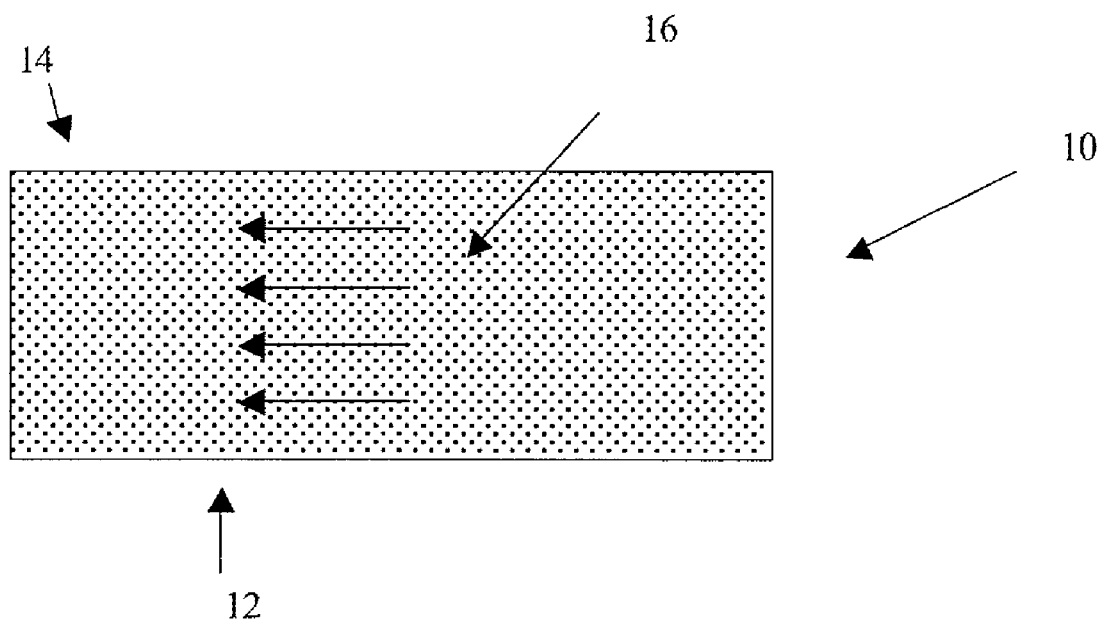
FIGS. 1A and 1B provide generalized representations of two different types of porous applicators found in fluid delivery devices of the subject invention.

Fluid delivery devices having a porous applicator, as well as methods for using the same in the highly localized delivery of fluid to a target site, are provided. The subject devices have a porous applicator through which fluid must flow in order to contact the target delivery site. The subject devices find use in a variety of fluid delivery applications in which the localized delivery of a fluid to a target site is desired. Also provided are systems and kits that include the subject fluid delivery devices.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

As summarized above, the present invention provides fluid delivery devices and methods for their use that provide for highly localized fluid delivery to a target site, particularly an internal physiological target site. In further describing the subject invention, the fluid delivery devices are described first in greater detail, followed by a review of methods of using the devices in localized fluid delivery, as well as kits and systems that find use in practicing the methods.

Fluid Delivery Devices—General Features

As summarized above, the subject invention provides fluid delivery devices for the localized delivery of a fluid to a target site of a subject, i.e., a physiological target site, where the target site may be an internal target site or an external target site. By target site is meant a specific region, location or area of a subject, where the term "subject" is used to refer to an animal, e.g., reptile, bird, mammal, etc, where the subject is usually a mammal, e.g., a primate, ungulate (hoofed animal, such as cow, horse, sheep, pig) dog, cat, etc., where the subject is, in many embodiments, a primate and often a human. In providing for localized delivery, the subject devices also remove fluid from the target site. A feature of the subject devices is the presence of a porous applicator through which fluid must flow during fluid delivery/target site contact in order to contact the target site.

The subject fluid delivery devices are characterized by having at least the following elements: (a) a porous applicator; (b) a fluid delivery element; and (c) an aspiration element. These elements work in concert to provide for highly localized and controlled delivery of fluid to a target site, be the target site an internal or external target site. Each of these features are now described separately in more detail.

Porous Applicator

The porous applicator is a porous structure that serves as a metering structure for the fluid and limits the region of the target site that the fluid contacts upon administration or delivery, thereby providing for highly localized fluid delivery. The region of porosity, e.g., porous tip, has a porosity that provides for the desired contact of fluid with the target site of the subject while at the same time limiting the flow of fluid into non-target sites proximal to the target site. The porosity of the applicator may be constant or variant, i.e., it may be the same throughout the applicator or vary between different regions of the applicator, e.g., a porous gradient may be present. Typically, the porosity of the porous region ranges from about 20 to 1,000µ, usually from about 30 to 250µ and more usually from about 35 to 70µ. In many embodiments, the porosity of the applicator is selected to provide for a flow rate through the applicator that ranges from about 0.1 ml/hr to about 100 l/hr, usually from about 600 ml/hr to about 3 l/hr.

The porous applicator may have a number of different configurations, depending on the target site with which it is to be employed and the particular application in which it is to be employed. For example, in certain embodiments, e.g., the porous applicator has a configuration that is tailored in shape with respect to the target site. For example, in the representative embodiment designed for use in delivery a fluid to an aortic valve leaflet, the porous applicator may be shaped to fit inside of, and contact substantially the entire surface area of, an aortic sinus. Alternatively, the porous applicator may be shaped like a scalpel blade or spatula where the target fluid delivery site is a tissue crevice or analogous structure. In yet other embodiments where the porous applicator is part of a delivery device designed for delivery of fluid to an internal vascular site from a remote external point, such as the catheter embodiments of the subject invention described in greater detail below, the porous applicator may be shaped like a cylinder or other analogous configuration through which fluid must flow to contact the target site. The above examples are merely representative, it being readily apparent to those of skill in the art that the porous applicator may be configured in any convenient manner with respect to the target fluid delivery site and still come within the scope of the present invention.

A given device may have a single porous applicator or multiple applicators, where the applicators may or may not be part of distinct fluid contact elements, as described in greater detail below. For example, in certain of the representative embodiments described below, the devices have three separate applicator/fluid contact elements—one for each valve leaflet of the aortic valve. The porous applicator/fluid contact element(s) may or may not be detachable from the remainder of the device, depending on the nature of the particular and recommended protocol for its use. For example, in certain embodiments, the porous applicators are detachable from the remainder of the device and, during use, are fitted into the device, as described in greater detail below.

While the particular dimensions and shape of the porous applicator may vary greatly depending on the nature of the target site, device and fluid to be delivered, as well as procedure being practiced, the porous applicator will generally have an overall mass that ranges from about 0.1 to about 1 kg, usually from about 1 g to about 100 g and more usually from about 5 g to about 50 g.

As indicated above, the porous applicator is located in the device at a position that requires the fluid to flow through the porous applicator in order to contact the target site. Therefore, the porous applicator is typically positioned at the distal end (i.e., the end furthest from the operator of the device or closest to the target site during use) of a fluid delivery device.

Figure 1B:
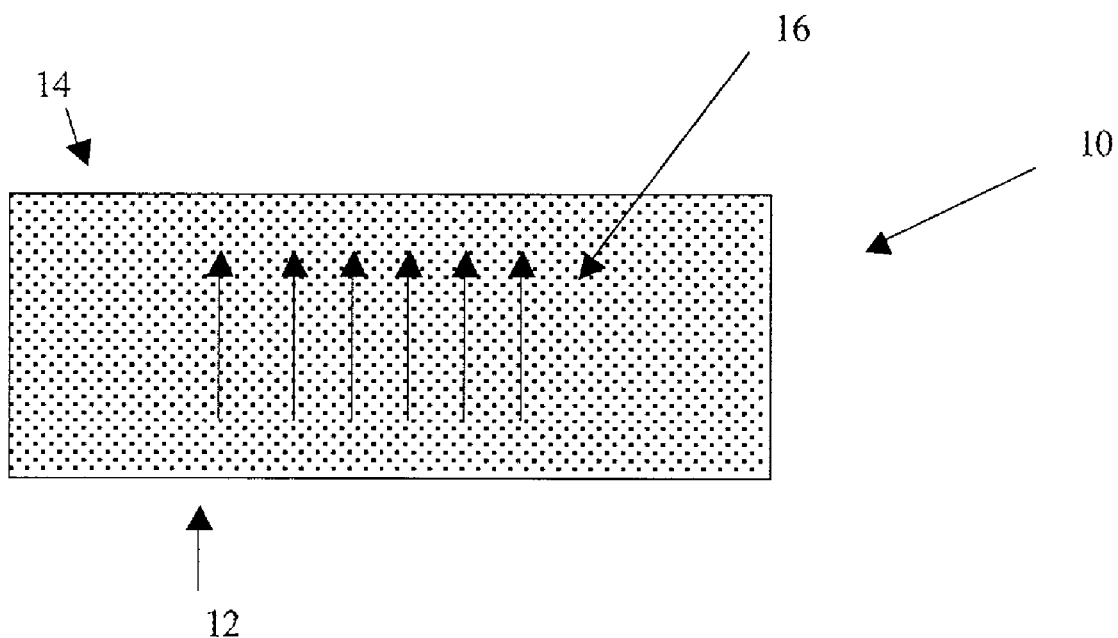

In certain device configurations, fluid flow through the applicator is parallel to the distal end of the applicator that contacts the target site, such that the fluid applicator is a porous fluid flow path and the sides of the flow path contact the target site during fluid delivery. This configuration is illustrated in FIG. 1B, where fluid flow through the applicator 10 is parallel to the distal end 14 of the applicator, as indicated by arrows 16. In this configuration, as fluid flows in the direction of arrows 16, the fluid along the distal edge 14 of the applicator 10 contacts the target site with which the distal end or edge 14 of the applicator is adjacent. This embodiment ensures that fresh fluid is always contacted with the target site.

In other device configurations, the porous applicator is configured in the device such that fluid flows through the applicator in a direction normal to the distal end of the applicator that contacts the target site during fluid delivery. In other words, fluid flows through the entire applicator in a direction towards the distal end of the applicator. FIG. 1A provides a representation of the fluid flow through the applicator in these embodiments. In FIG. 1A, porous applicator 10 has a proximal end 12 and a distal end 14, where the distal end 14 is the end that contacts the target site during fluid delivery. Arrows 16 indicate the direction of fluid flow through the applicator, i.e., in a direction normal to the distal end 14 of the applicator.

Whether the device is configured for fluid to flow parallel with or normal to the distal end of the applicator varies with respect to the particular device configuration and the intended application for which the device is designed to be used. Representative embodiments of each of these configurations are provided in greater detail below.

The porous applicator is fabricated from any convenient porous material. Porous materials of interest include polymeric materials, e.g., plastics such as polyethylene, PTFE, etc.; metals, e.g. stainless steal, etc., composite materials; and the like, where in principle the porous applicator may be fabricated from any convenient, physiologically compatible material that is also compatible with the fluid that is delivered through it. In certain embodiments, the porous applicator is fabricated from a compliant material, which provides for a certain degree of compliance upon contact with the target delivery site, thereby providing for further control over the region with which fluid is contacted, such that the porous applicator makes a flush juxtaposition with the target tissue upon contact with the target site, much like a sponge conforms to a surface upon which it is placed. In many of these embodiments, the compliant material from which the applicator is fabricated is a polymeric material.

In yet other embodiments, the porous applicator is fabricated from a material that is "harder" than a material which has a Mohs scale rating of 5; e.g., it has a "hardness" that is at least about 6 on the Mohs scale, such that its hardness is at least that of orthoclase. As such, the material is a material that is capable of physically modifying, e.g., scratching or deforming the surface of, an apatitic structure upon contact with the apatitic structure, without itself being modified. Representative materials from which the applicator is fabricated in these particular embodiments are metals, e.g., stainless steel and other physiologically compatible metals.

The porous applicator may also be a composite or hybrid structure that includes both permeable and impermeable regions.

However, in many preferred embodiments, the porous applicator is fabricated from a compliant material, which provides for the ability to conform the applicator to the target site during use and therefore better localize fluid delivery, as discussed above. For purposes of convenience, the inventive device are now further described in terms of this preferred embodiment.

Fluid Delivery Element

In addition to the porous applicator, the subject devices also include a fluid delivery element that conveys fluid to the applicator from a fluid source. The fluid delivery element may be any convenient fluid conveyance structure, and in many embodiments is a tube or analogous structure, e.g., an elongated structure having a lumen therein through which fluid can flow. The fluid delivery element is typically an elongated structure and has a distal and proximal end, where the distal end of the fluid delivery element is in fluid communication with the proximal end of the porous applicator element, as described above. The proximal end of the fluid delivery element is, at least during use, in fluid communication with a source of fluid to be delivered to the target site, e.g., a fluid reservoir containing the to be delivered fluid.

While the fluid delivery element is an elongated structure, its length may vary greatly depending on the particular type of device, e.g., whether the device is a "hand-held" device for use in open surgery or a catheter device for use in percutaneous fluid delivery applications. (As used herein, the term "open surgical" is employed to describe protocols in which the surgeon has direct, visual access to the target site; while the term "percutaneous" refers to protocols in which the surgeon does not have direct visual access to the target site, but instead employs a visualization means, such as a fluoroscopy scanning device).

As such, the length of the device may range from about 10 to about 300 cm, often from about 20 to about 200 cm. In many hand-held embodiments intended for use in open surgical applications where remote access is not required, the length of the fluid delivery element often ranges from about 10 cm to about 50 cm, usually from about 20 cm to about 30 cm. In many catheter embodiments where the device is intended for percutaneous access, the length of the fluid delivery element typically ranges from about 50 cm to about 300 cm, usually from about 100 cm to about 200 cm.

The fluid delivery element is configured to provide for the desired flow rate of fluid to the porous applicator. As such, this element is configured to provide for a flow rate that typically ranges from about 0.1 ml/hr to about 10.0 l/hr, usually from about 600 ml/hr to about 3 l/hr. In many embodiments where this element includes a fluid delivery lumen, e.g., inside of a tube or analogous structure, the inner diameter of the lumen typically ranges from about 0.25 mm to about 10 mm, usually from about 0.5 mm to about 2 mm.

Aspiration Element

The subject fluid delivery devices typically further include a fluid aspiration element that provides for removal of fluid from the target site and/or flow of the fluid through the porous applicator (e.g., in those applicator embodiments where fluid flow is perpendicular to the distal end that contacts the target site). As such, the subject devices may be viewed as devices that locally flush a target site with a fluid, such that the target site is constantly contacted with fresh fluid by the fluid delivery device. The fluid aspiration element is generally a fluid flow path (or collection of fluid flow paths) that has one or more openings through which fluid, as well as gases and debris, may flow away from at least the vicinity or region of the target site and/or distal end of the device, e.g., the distal/contact end of the porous applicator and therefore target site, where the flow path may be connected to a negative pressure element, e.g., a vacuum, to provide for a sufficient force to pull fluid away from the target site through the aspiration element. In certain embodiments, the opening (or openings) of the fluid aspiration element has an effective total cross-sectional area that is sufficiently large to remove fluid, and debris, from the vascular site.

Second Fluid Delivery Element

In certain embodiments, the subject devices include a second fluid delivery element, e.g., a buffer delivery element, as described in greater detail below. This second fluid delivery element may be present in a variety of different locations in the device, depending on how fluid delivery from this element is desired relative to the delivery of fluid by the porous applicator.

Fluid Driving Element

In certain embodiments, the device includes an element which serves to drive fluid out of the porous applicator. In many such embodiments, this fluid driving element is a mechanical element, that mechanically drives fluid out of the porous applicator, and consequently into the target site with which the porous applicator is in contact. Of particular interest are mechanical driving elements that compress the porous applicator to drive fluid out of the porous applicator. In certain of these embodiments, the mechanical driving element provides for a cyclical compression and expansion of the porous applicator, such that fluid is cyclically driven out of and then drawn back into the porous applicator, where these embodiments are useful in ensuring that fresh fluid is repeatedly driven into the target site. A variety of different mechanical fluid driving elements may be employed, such as expandable balloons placed beneath the porous applicators, a spring element that can be expanded and contracted, and the like. Any convenient such element may be employed.

External Energy Application Element

In certain embodiments, external energy application elements are included in the devices, e.g., to apply external energy to the target site (e.g., aortic valve) to promote mechanical break-up of the calcified deposits into particles or debris that can be easily removed from the vascular site. Any technology of applying external energy to the target site may be present on the subject devices. As such, jets or other such technologies that are capable of providing varying external forces to the target deposits to cause the target deposit to break up or disrupt may be employed. Of particular interest in many embodiments is the use of sonic energy, where sonic energy of interest includes infrasound, audible sound and ultrasound. The sonic energy, e.g., ultrasound, can be applied during the entire time of contact of the cardiovascular tissue with the acidic treatment solution, or it can be applied for only part of the treatment period. In one embodiment, the sonic energy is applied for several short periods of time while the dissolution treatment solution is contacted with the target occlusion. Sonic energy elements that are suitable for use with the subject methods are known and readily available to those of skill in the art. For example, U.S. Pat. Nos.: 5,695,460; 5,997,497; 6,047,700; 6,083,573; 6,113,570; and 6,308,714; as well as the United States patents cited therein; all describe various ultrasound technologies for delivering ultrasound to a physiological, including cardiovascular, site, where such technologies include transdermal delivery technologies. The disclosures of each these patents as well as those cited therein with respect to their discussions of ultrasound delivery technologies are herein incorporated by reference. Also of interest are mechanical means of applying external energy. Mechanical means of interest include moving structures, e.g. rotating wires, guidewires, which physically contact the target lesion and thereby apply physical external energy to the target lesion.

Additional Features

The subject fluid delivery devices are further characterized by being capable of being attached at their proximal ends, either directly or through one or more attachment means, to a fluid reservoir, e.g., an acidic dissolution fluid reservoir, a pharmacological agent fluid reservoir, etc. In many embodiments, the proximal end of the device is further characterized by having a means for attaching to a vacuum or negative pressure element that provides for aspiration of fluid through the aspiration element of the device. Typically, the above described attachment element(s) is a manifold or similar structure, which may or may not be equipped with various valves, as is known in the art.

Methods of Fabrication

The above fluid delivery devices may be fabricated using an convenient protocol, where protocols that may be used to fabricate the devices, including extrusion, micromachining (e.g., laser drilling), etc., are known and readily practiced by those of skill in the art.

Fluid Delivery Devices

Specific Embodiments

As indicated above, a variety of different embodiments of the subject localized fluid delivery devices are provided. Common to each of these embodiments is the presence of a porous applicator, as described above. The devices can be further characterized as two different types: (a) one in which the porous applicator provides for fluid flow through the applicator in a direction parallel to the distal end of the applicator such that the porous applicator is a porous fluid flow path, e.g., as shown in FIG. 1A; and (b) one in which the porous applicator provides for fluid flow through the applicator in a direction normal to the distal end, e.g., as shown in FIG. 1B. The following section provides descriptions of several different representative embodiments of the subject fluid delivery devices.

Porous Applicator—Porous Fluid Flow Path Devices

In this category of fluid delivery devices according to the subject invention, the porous applicator is actually a porous fluid flow path in which fluid flows parallel to the edge of the applicator that contacts the target site during. This flow path is illustrated in FIG. 1A, as described above. In this category of devices, fluid flows through the porous applicator from the distal end of a fluid delivery element and into an aspiration element, which provides for the flow of fluid through the porous flow path, i.e., aspiration draws the fluid from the distal end of the fluid delivery element through the flow path of the porous applicator.

A wide variety of different fluid delivery devices come within the scope of this broad category, where such devices include non-catheter or open-surgical devices, e.g., hand-held devices, as well as percutaneous, e.g., catheter based devices, such as those that might be used in a percutaneous approach, e.g., for beating heart surgery applications, etc. A representative specific open-surgical device for use in contacting aortic valve leaflets as well as associated structures of aortic roots with a fluid is now described further as representative of devices falling within this first category.

Aortic Valve Fluid Delivery Devices

One representative localized fluid delivery device of the subject invention is a device for contacting aortic valve leaflets with a fluid, such as a demineralization fluid, as described in greater detail below. The device described below is described in terms of a hand-held, open-surgical device that is employed in open surgical procedures. However, those of skill in the art will appreciate that the structures can be readily adapted for a catheter-based device for use in percutaneous procedures, such as may be employed in beating heart operations.

Figure 2:
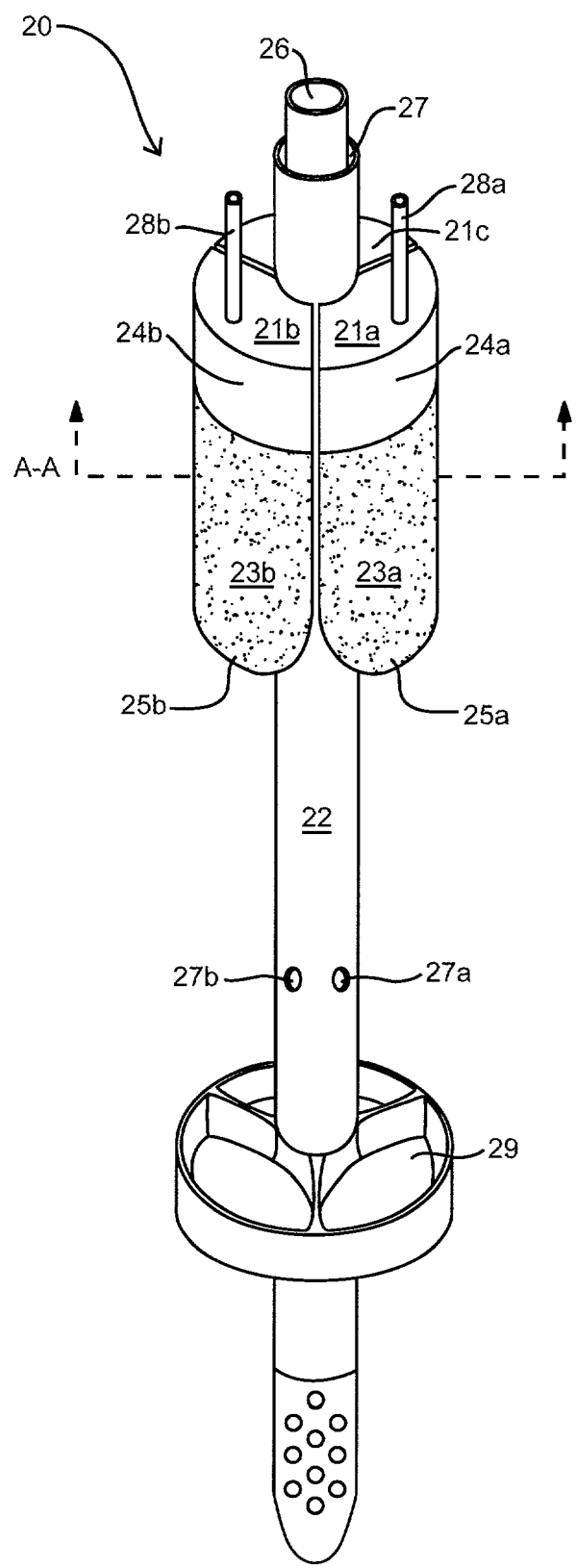
FIG. 2 provides a three-dimensional view of the distal end of a representative embodiment of a device according to the present invention.

A representative embodiment of an aortic valve leaflet fluid delivery device is depicted in FIG. 2. In FIG. 2, localized fluid delivery device 20 is configured to allow for blood flow through an aortic valve while providing for highly localized fluid delivery to the aortic side of the aortic valve leaflets. To provide for these functions, device 20 includes three distinct fluid contact elements 21a, 21b and 21c, arranged around a central shaft 22. Each fluid contact element (21a,b and c) is made up of a porous applicator (23a, 23b) present on an impermeable backing (24a and 24b). Fluid delivery elements 28a and 28b provide for delivery of fluid from a fluid source to the porous applicators 23a and 23b respectively. The distal tips (25a and 25b) of the fluid contact elements are configured to fit snugly or flushly inside of an aortic sinus and therefore provide for precise contact with the aortic valve leaflets. The central shaft 22 provides structure for the fluid delivery elements and houses a shunt 26 that provides for blood flow from the ventricle during use. The shunt is centrally or axially located inside shaft 22 such that the two elements are concentric. The space between the outer surface of the shunt and the inner surface of shaft 22 defines an aspiration lumen 27 that is the aspiration element of the device. Fluid enters the aspiration lumen 27 through aspiration ports 27a and 27b located on shaft 22. Also depicted in FIG. 2 is valve occluder 29. Valve occluder fits flush with the ventricular side of the aortic valve leaflets during use and serves to further isolate the valve leaflets and localize the area of leaflets that are contacted with the fluid. While the ventricular side valve occluder 29 is depicted as a solid structure in FIG. 2, this element may also be a balloon or other occlusive device. See e.g., the alternative embodiment depicted in FIGS. 7A and 7B, which embodiment shows a balloon.

Figure 3:
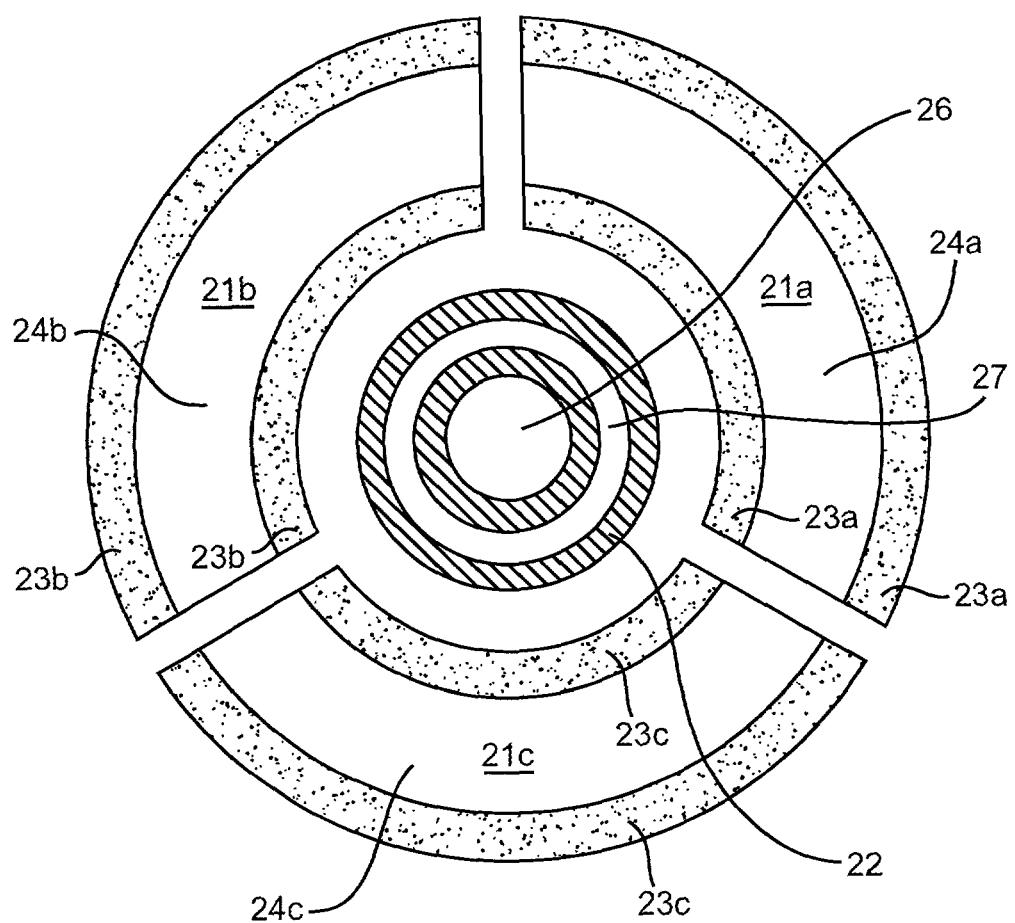
FIG. 3 provides a view along line A-A of FIG. 2.

FIG. 3 provides a cross-sectional view of the device shown in FIG. 2 along line A-A. In FIG. 3, fluid contact elements 21a, 21b and 21c are concentrically positioned around the outer surface of shaft 22. Concentrically positioned inside of shaft 22 is shunt 26. FIG. 3 also shows how each porous applicator (23a, 23b and 23c) is wrapped around an impermeable backing element (24a, 24b and 24c), that makes the porous applicator elements porous fluid flow paths through which fluid flows in a direction parallel to the edge of the applicator that contacts the target valve site during use, as illustrated in FIG. 1A.

Figure 4:
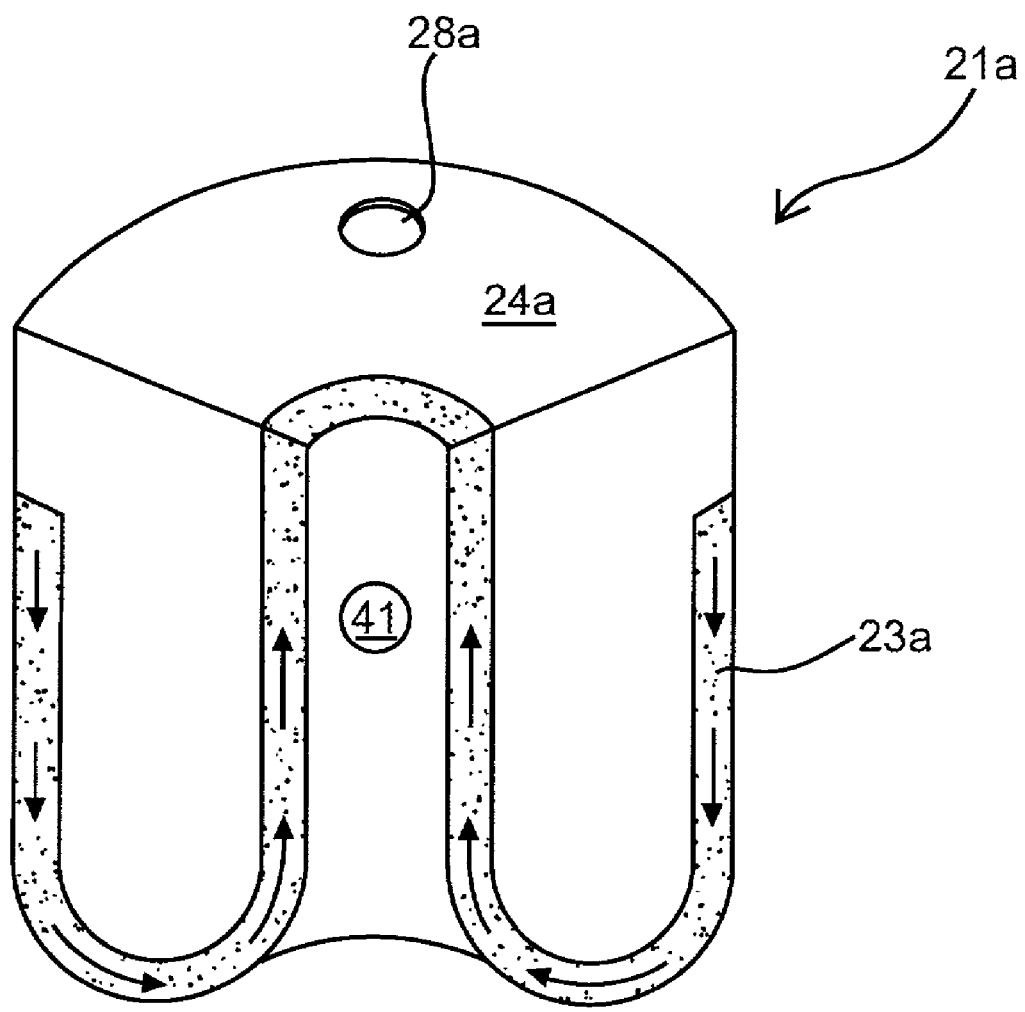
FIG. 4 provides a three-dimensional view of an individual fluid contact element configured to fit inside of an aortic sinus of an aortic valve.

FIG. 4 provides a cross-sectional view of a single fluid contact element 21a. Fluid contact element 21a includes porous applicator 23a which wraps around the distal end of impermeable backing 24a, thereby making a porous fluid flow path around the distal end of the fluid contact element. Also depicted is fluid delivery element 28a. Positioned inside of contact element is aspiration location 41. Aspiration is applied to this region, which aspiration results in fluid flow through the porous applicator (porous fluid flow path) in the direction depicted by the arrows.

Figure 5:
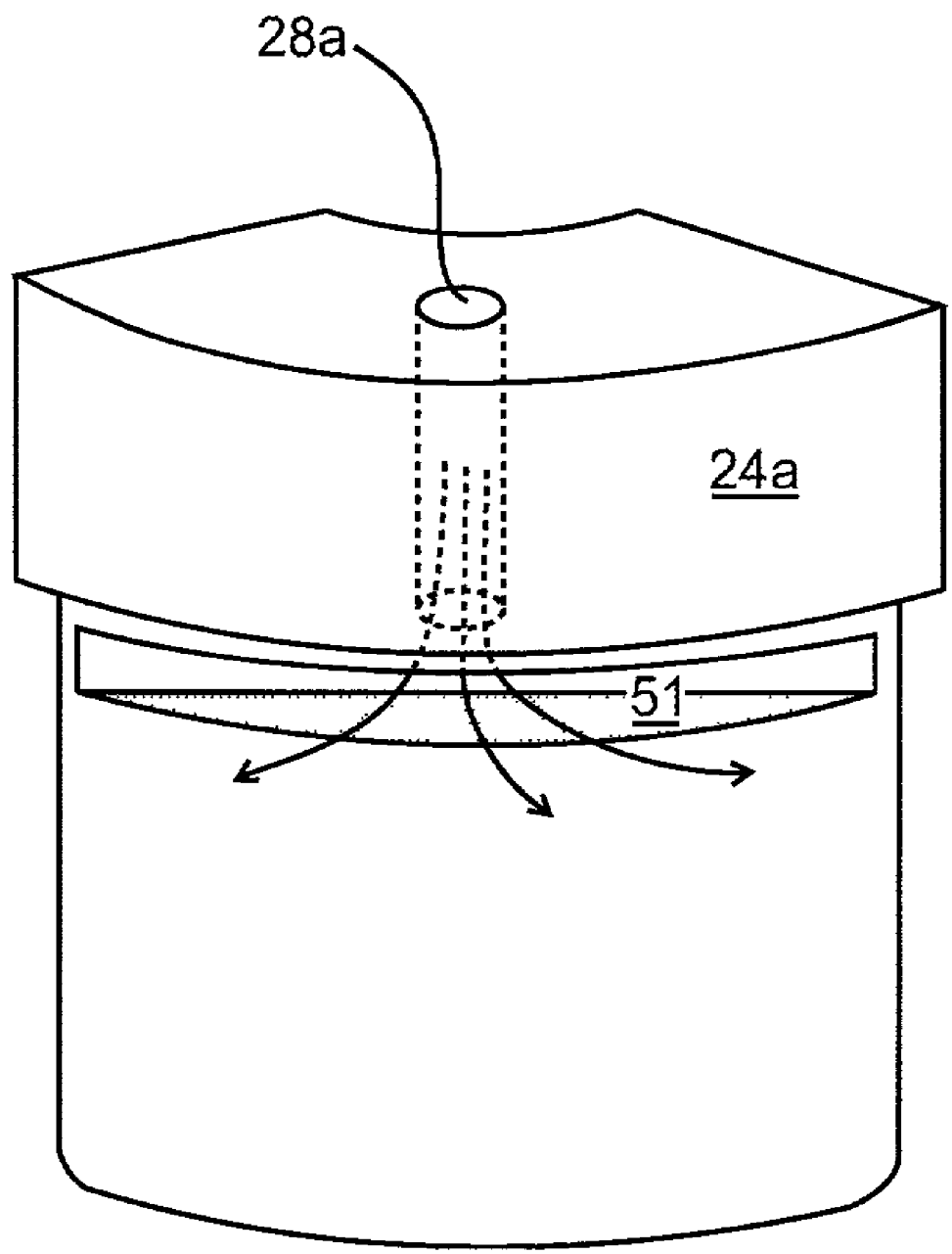
FIG. 5 provides a three-dimensional view of an impermeable backing element of the fluid contact element depicted in FIG. 4.

FIG. 5 provides a three-dimensional illustration of the impermeable backing element 24a of fluid contact element 21a. Impermeable backing element 24a includes fluid delivery element or tube 28a which exits at exit port 51 to enter the porous applicator 23a (not shown). The impermeable backing element may be fabricated from any convenient material, so long as it is fluidically impermeable, e.g., non-porous. In certain embodiments, an impermeable yet compliant material is desired, where representative materials include impermeable foam materials or permeable foam materials that have been coated with an impermeable coating so as to render them impermeable, where such coatings include, but are not limited to: parylene, vinyl, urethane, etc.

Figure 6:
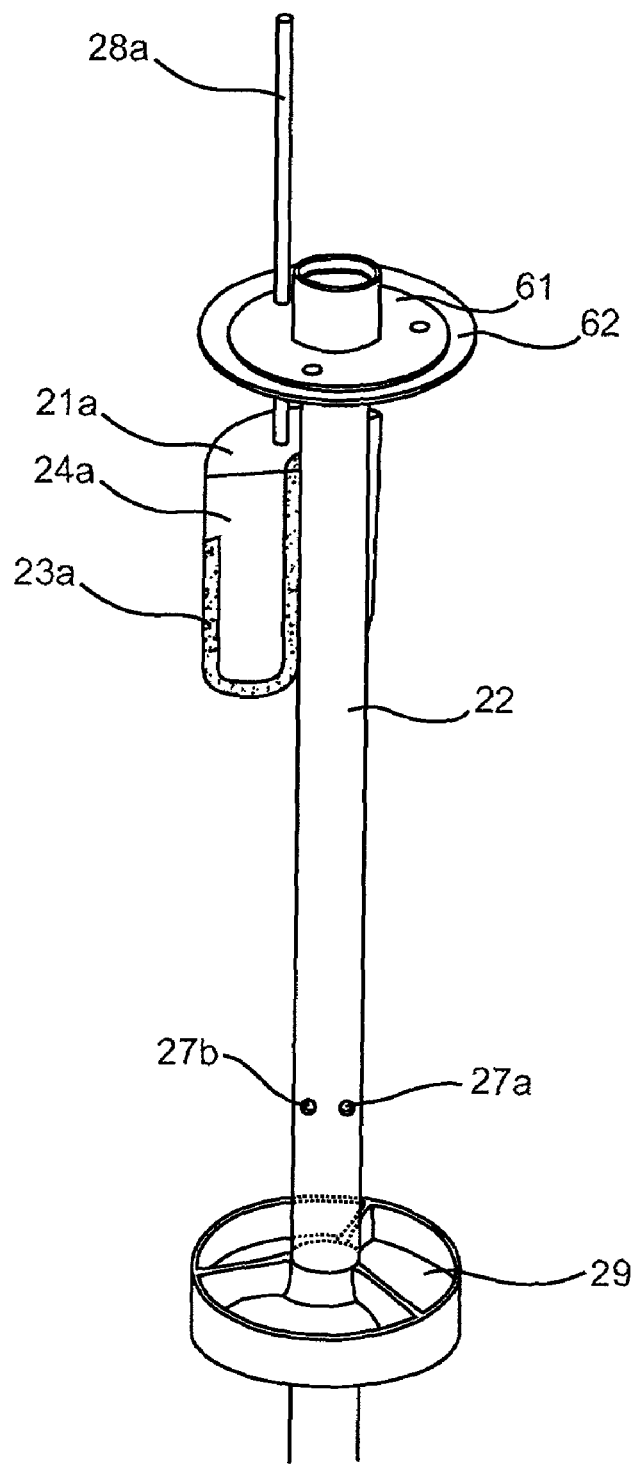
FIG. 6 provides another cutaway three-dimensional view of the device shown in FIG. 2.

FIG. 6 provides yet another view of the device shown in FIG. 2. Also visible in FIG. 6 is cap structure 61 that, during use, is compressed on top of fluid contact elements 21a to 21c to ensure a flush contact of the contact elements with the target valve leaflet sites. Cap structure 61 rests on top of sealing element 62, which is any convenient sealing material, e.g., polymer, gel, etc. The device may include a locking mechanism to maintain the cap in position when compressed on top of the contact elements, where any convenient locking mechanism may be employed.

Figure 7A:
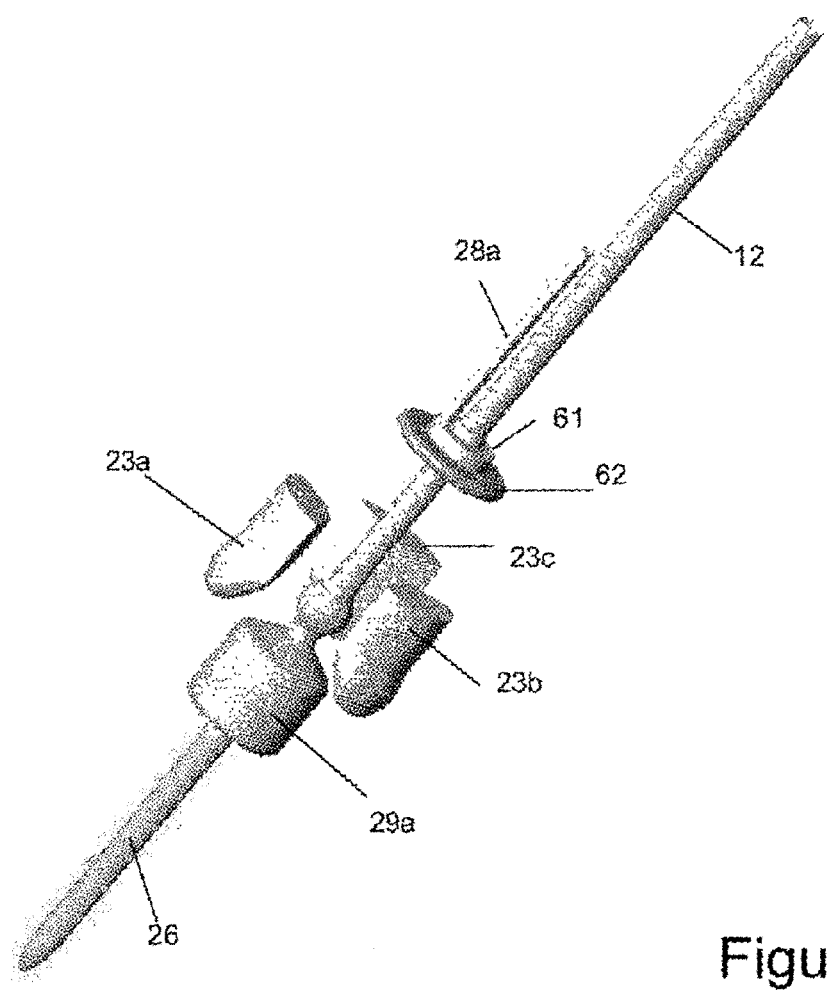
FIGS. 7A and B provide view of an alternative embodiment of an aortic valve treatment device according to the subject invention, where the fluid contact elements are detachable from the remainder of the device.
Figure 7B:
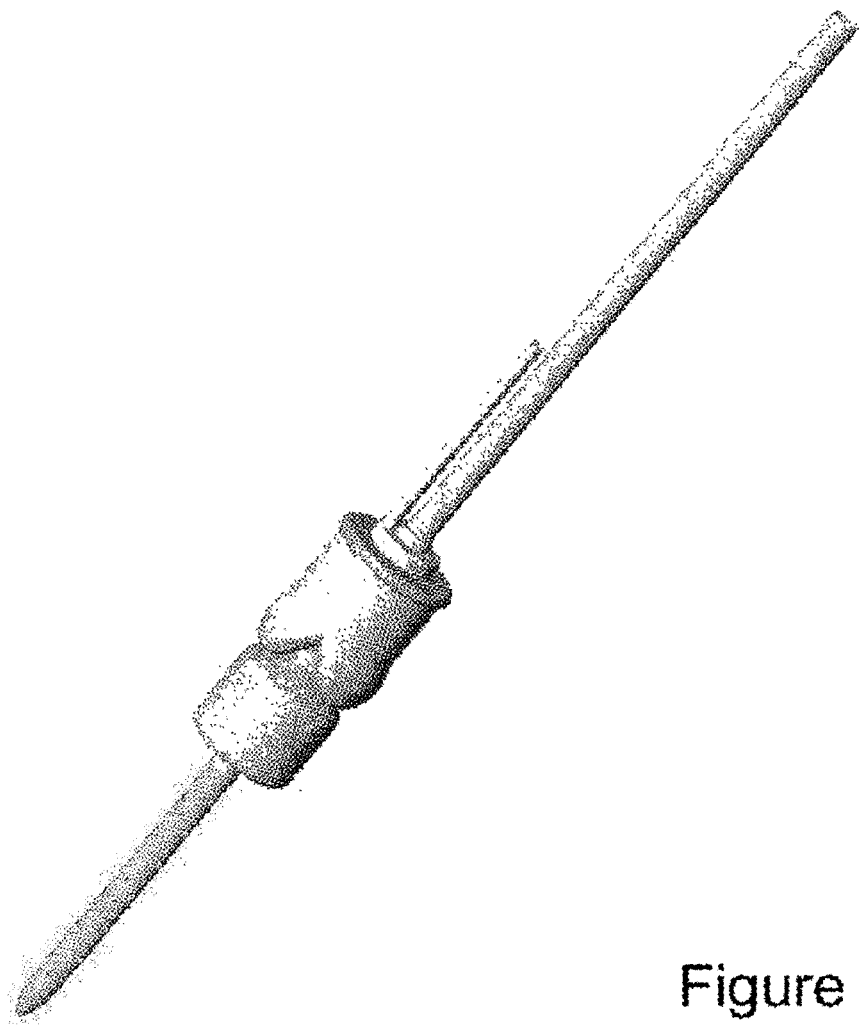

FIGS. 7A and 7B provide three dimensional views of an alternative embodiment of the device shown in FIG. 1, wherein the ventricular side occlusive device is an inflateable balloon 29a. In addition, in this embodiment, the fluid contact elements are detachable from the remainder of the structure and, during use (as described in detail below) are positioned between the cap element 62 and ventricular occlusive balloon 29a in manner that provides for tight contact of the porous applicator of the fluid contact elements with the valve leaflets.

The above described first embodiment is particularly suited for use in contacting aortic valve leaflets with a fluid in a highly localized manner.

Porous Applicator—Porous Tip Devices

As summarized above, also coming within the scope of the invention are porous applicators in which fluid flows normal to the distal or target site contact edge of the applicator, as illustrated in FIG. 1B. A feature of the subject fluid delivery devices of this broad category is that the porous applicator is located at the distal end of at least one of the fluid delivery paths or lumens of the device. As such, a porous member or element is positioned at the distal end of at least a first fluid flow lumen of the device. The distally located porous applicator(i.e., region of porosity) is positioned at the distal end of the at least first fluid flow lumen such that fluid must flow through the porous region in order to exit the fluid flow lumen through its distal end and reach the target site, such as an internal body site, e.g., target vascular site. The region of porosity of the device may extend for substantially the entire length of the fluid delivery device or a substantial portion thereof, e.g., 50%, 75% 90%, or even 100%, but in many embodiments is confined to the distal region of at least the first fluid flow path lumen, e.g., the distal most 10%, 5%, 1%, or smaller length percentage, of the device. In these latter typically preferred embodiments, the distally located region of porosity is properly viewed as a distally located porous tip through which fluid must flow in order to exit the distal end of the fluid delivery device in a manner as depicted in FIG. 1B.

In certain embodiments, the region of porosity is present only at the distal end of the first fluid delivery lumen. In yet other embodiments, one or more additional fluid flow lumens, e.g., the aspiration lumen and/or the second fluid delivery lumen when present, may include a region of porosity at their distal end. The region of porosity may take the form of a porous tip or plug that is present at the distal end of the lumen, as a covering of porous material that covers the distal end of the lumen, etc., whichever is convenient.

As with the first broad category of devices, a wide variety of different fluid delivery devices come within the scope of this second broad category, where such devices include non-catheter or open-surgical devices, e.g., hand-held devices, as well as percutaneous, e.g., catheter based devices. Several of these representative embodiments are now further described.

Second Representative Embodiment

Figure 8:
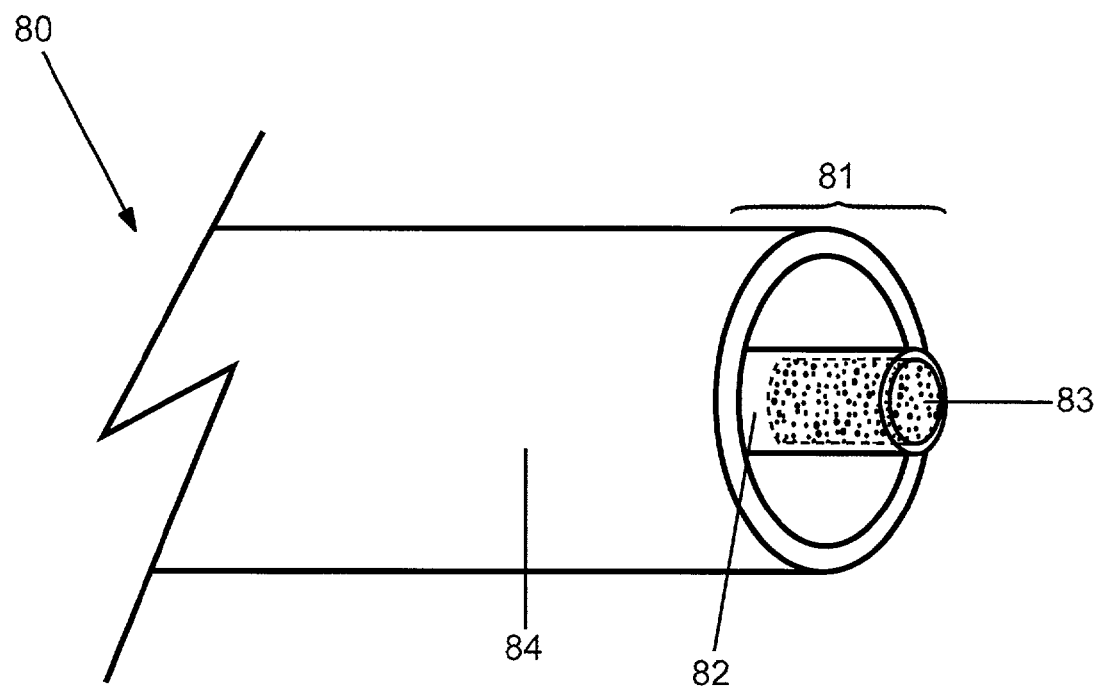
FIG. 8 provides a view of a fluid delivery device according to a second embodiment of the subject invention.

One representative embodiment of the subject fluid delivery devices has a distal end with a configuration as shown in FIG. 8. In this embodiment, the delivery device includes a fluid delivery lumen and an aspiration lumen that have a coaxial configuration. The fluid delivery lumen has a distal porous applicator or tip that is present inside of, and along the axis of, an aspiration lumen, as shown in FIG. 8, such that the fluid introduction lumen and the aspiration lumen are concentric and share the same central axis.

More specifically with respect to FIG. 8, distal end 81 of the fluid delivery device or catheter 80 includes fluid delivery lumen 82 and aspiration lumen 84. Located at the end of fluid delivery lumen 82 is porous applicator 83, though which fluid must flow in order to exit fluid delivery lumen 82 of the distal end of the device 80.

While dimensions of the various components may vary depending on the particular target site, in many embodiments the outer diameter of the aspiration lumen ranges from about 1.0 to 10 mm, usually from about 1.0 to 5.0 mm and the inner diameter ranges from about 0.5 to 7.5 mm, usually from about 1.5 to 3.0 mm. The outer diameter of the fluid delivery lumen ranges from about 0.25 to 1.5 mm, usually from about 0.5 to 1.25 mm and the inner diameter ranges from about 0.2 to 1.0 mm, usually from about 0.4 to 0.9 mm. The length of the porous applicator ranges from about 1.0 to 1200 mm, usually from about 2.0 to 20 mm, and the diameter ranges from about 0.75 to 7.5 mm, usually from about 1.75 to 2.75 mm. The porous applicator has a porosity ranging from about 20 to 1,000μ, usually from about 35 to 70μ.

Third Representative Embodiment

Figure 9:
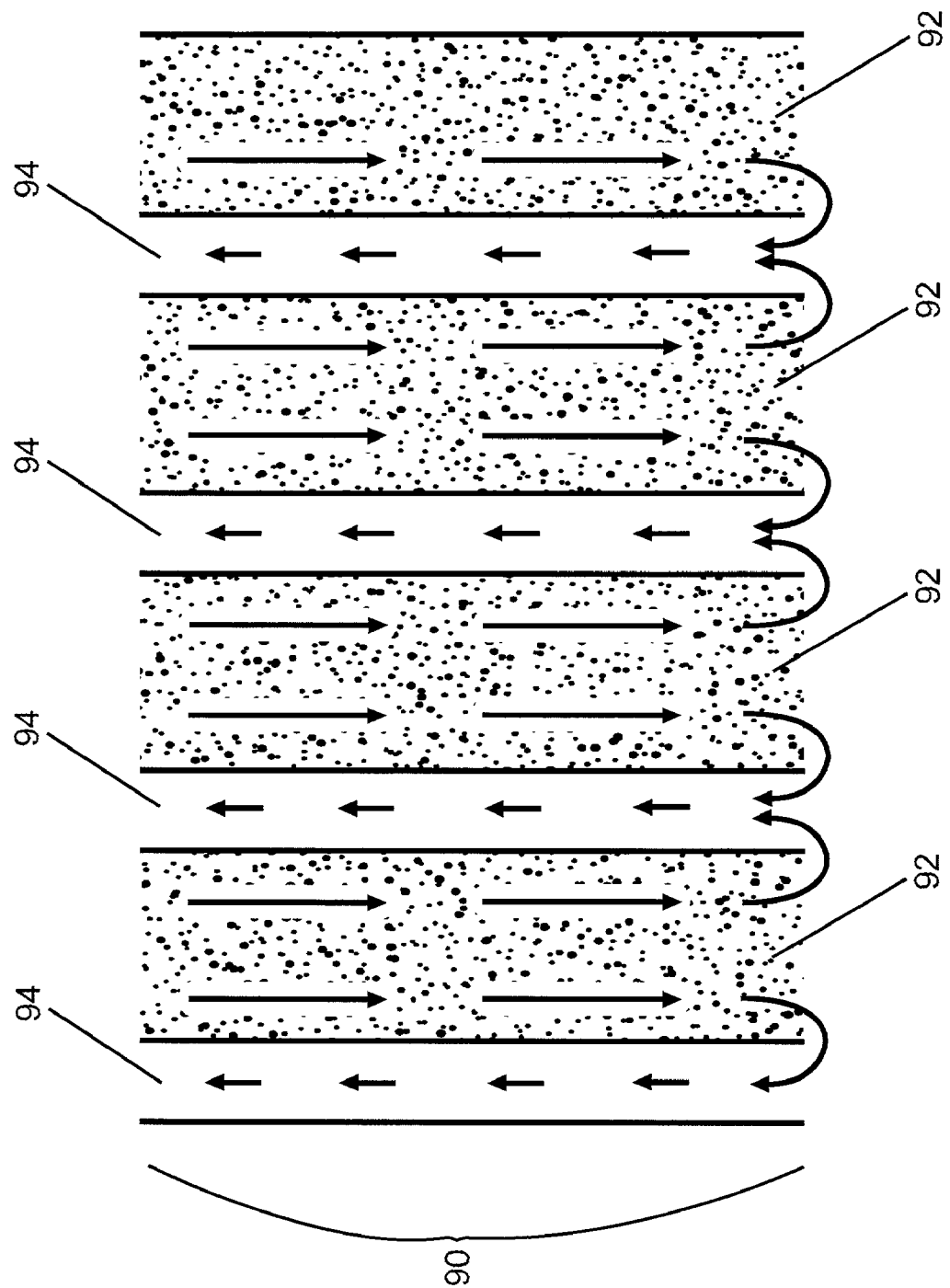
FIG. 9 provides a cross-sectional view of a fluid delivery device according to a third embodiment of the subject invention.

In another specific embodiment, the device includes a distal end that is made up of a plurality of aspiration flow paths and fluid delivery flow paths, where the fluid delivery flow paths include the region of porosity at their distal end, as depicted in FIG. 9. In FIG. 9, distal end 90 of the device includes a number of porous fluid introduction flow paths 92 and a number of fluid aspiration flow paths 94. In other words, the distal end includes a plurality of different fluid introduction lumens and aspiration lumens. By plurality is meant at least 2, usually at least 4 and more usually at least 5, where the number of flow paths may range from about 2 to 200, usually from about 5 to 100.

The distal end of the fluid delivery device of this embodiment may take a number of alternative configurations. In one configuration, the distal end is made up of a plurality of distinct fluid delivery lumens and aspiration lumens bundled together to produce the structure shown in FIG. 9. In an alternative embodiment, the distal end is made up of a single porous structure that seals the end of a fluid delivery element and through which multiple aspiration lumens are positioned, e.g., drilled. In these embodiments, each of the aspiration flow paths is a tube or analogous structure that extends from the distal end of the porous applicator or tip through the porous tip to a merging point, when present, at a point located some distance, typically at least about 1 mm, usually at least about 5 mm and more usually at leas about 10 mm, from the distal end of the device.

While the dimensions of the various flow paths and elements may vary depending on the target site for which the device is designed, in certain embodiments, the specifications of the device are the same as those described above for the first representative embodiment.

Fourth Representative Embodiment

Figure 10A:
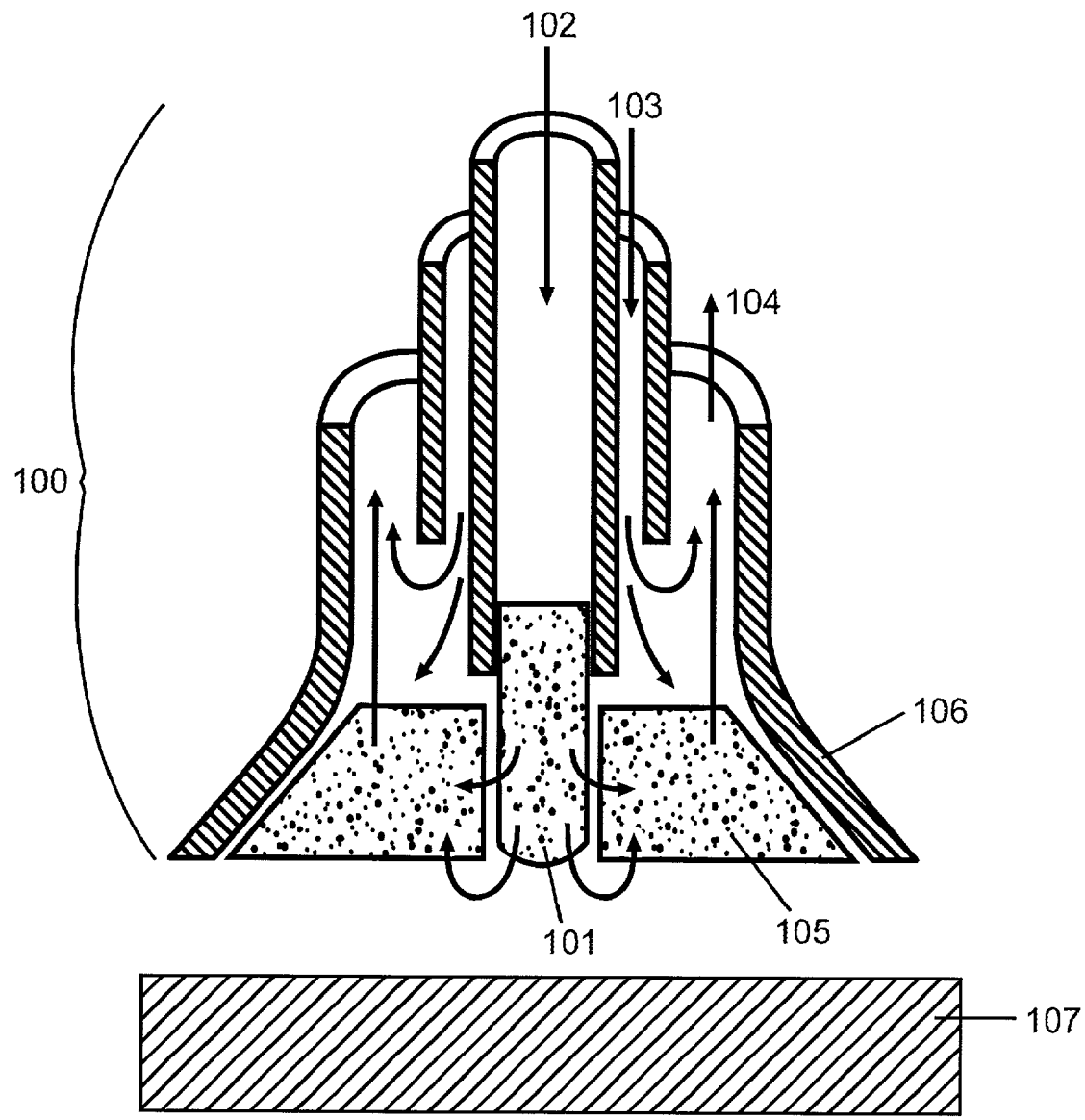
FIGS. 10A to 10D provide different views of a fluid delivery device according to a fourth embodiment of the subject invention.

FIGS. 10A to 10D depict a fourth representative embodiment of a fluid delivery device according to the subject invention. In FIG. 10A, a cross sectional view of the distal end 100 of a fluid delivery device that includes a first fluid delivery lumen 102 (e.g., for a low pH dissolution solution), a second fluid delivery lumen 103 (e.g., for a buffer solution) and an aspiration lumen 104 is provided. The three fluid lumens are concentric or coaxial such that they share a common central axis, with the first fluid delivery lumen 102 being present inside the second fluid delivery lumen 103, which in turn is present inside the aspiration lumen 104. Located at the distal end of first fluid delivery lumen 102 is porous applicator 101, which in certain embodiments is made up of a non-compliant or stiff porous material and configured to allow for mechanical manipulation of the target site (e.g., it is shaped like a spatula for accessing crevices). Also present in certain embodiments is a compliant porous material 105 that covers the openings of the second fluid delivery lumen and aspiration lumen. The distal walls of the outer aspiration lumen may be in the form of a flexible skirt 106 or analogous material that provides for a custom isolation area on the target site 107 during use.

Figure 10B:
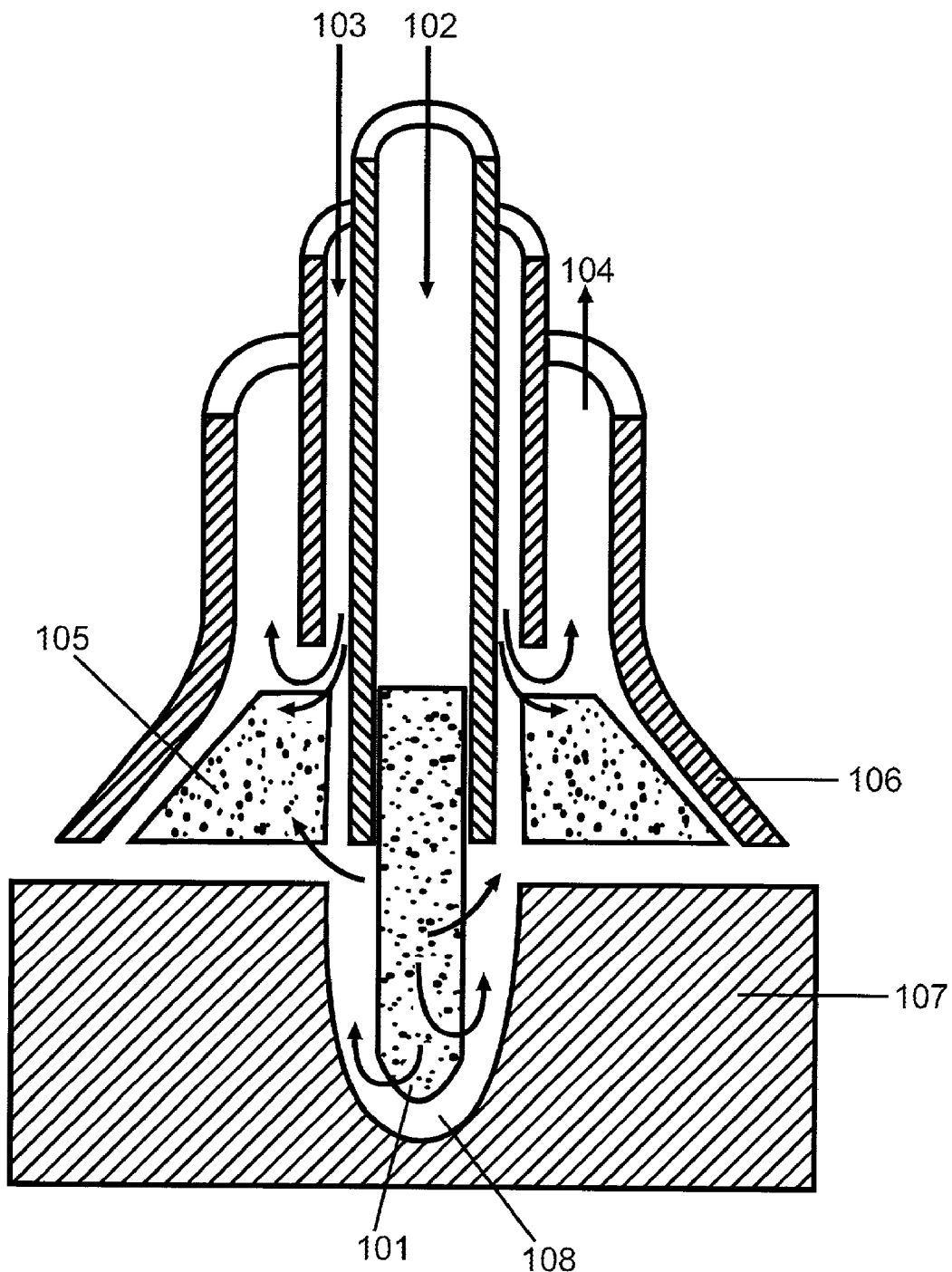

FIG. 10B provides a cross-section representation of the device of FIG. 10A delivering a fluid to a crevice 108 in a target vascular 37 site. In FIG. 10B, the distal end 101 is positioned against target site 107 and applicator 101 is moved into crevice 108. A first fluid, e.g., a low pH dissolution fluid, is then introduced into crevice 108 from lumen 102 by applicator 101. A second fluid, e.g., buffer, is concomitantly introduced via lumen 103. Fluid is withdrawn from the target site by aspiration lumen 104, which has a distal open end defined by the target site 107 and surround flexible skirt 106.

The dimensions of the various elements of this embodiment vary but in many embodiments fit within the following parameters. The inner diameter of lumen 32 ranges from about 0.1 to 10 mm, usually from about 0.5 to 7.5 mm, while the outer diameter ranges from about 1.0 to 15 mm, usually from about 1.0 to 10 mm. The inner diameter of second delivery lumen ranges from about 1.5 to 15 mm, usually from about 2 to 10 mm while the outer diameter ranges from about 2 to 20 mm, usually from about 2.5 to 11 mm. The inner diameter of the aspiration lumen ranges from about 2.5 to 22 mm, usually from about 3 to 12 mm, while the outer diameter ranges from about 3 to 25 mm, usually from about 4 to 13 mm. The length of the elongated porous applicator ranges from about 0.5 to 15 mm, usually from about 1.0 to 10 mm and has a porosity ranging from about 30 to 1000μ, usually from about 35 to 70μ.

Figure 10C:
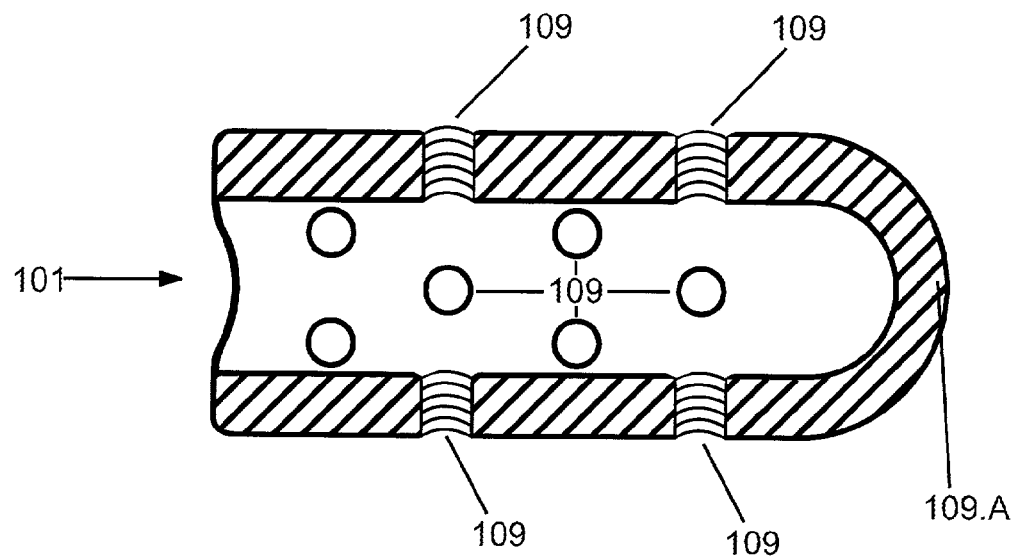
Figure 10D:
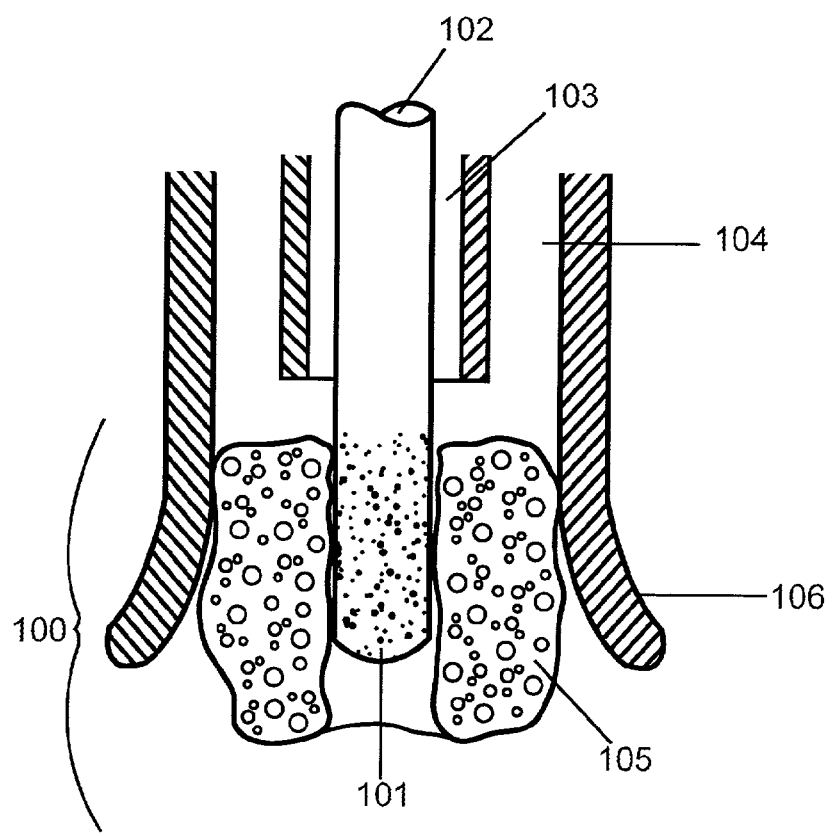

FIG. 10C provides a cross-sectional view of the distal end of one embodiment of a non-compliant porous applicator or tip 101. The porous applicator 101 has a sealed end 109A of the delivery lumen 102 into which a plurality of small holes or "pores" 109 have been created, which results in a porous structure of a non-compliant nature. FIG. 10D shows the above specific embodiment of the porous tip 101 positioned at the distal end 100 of a fluid delivery device represented by FIG. 10A.

Fifth Representative Embodiment

Figure 11:
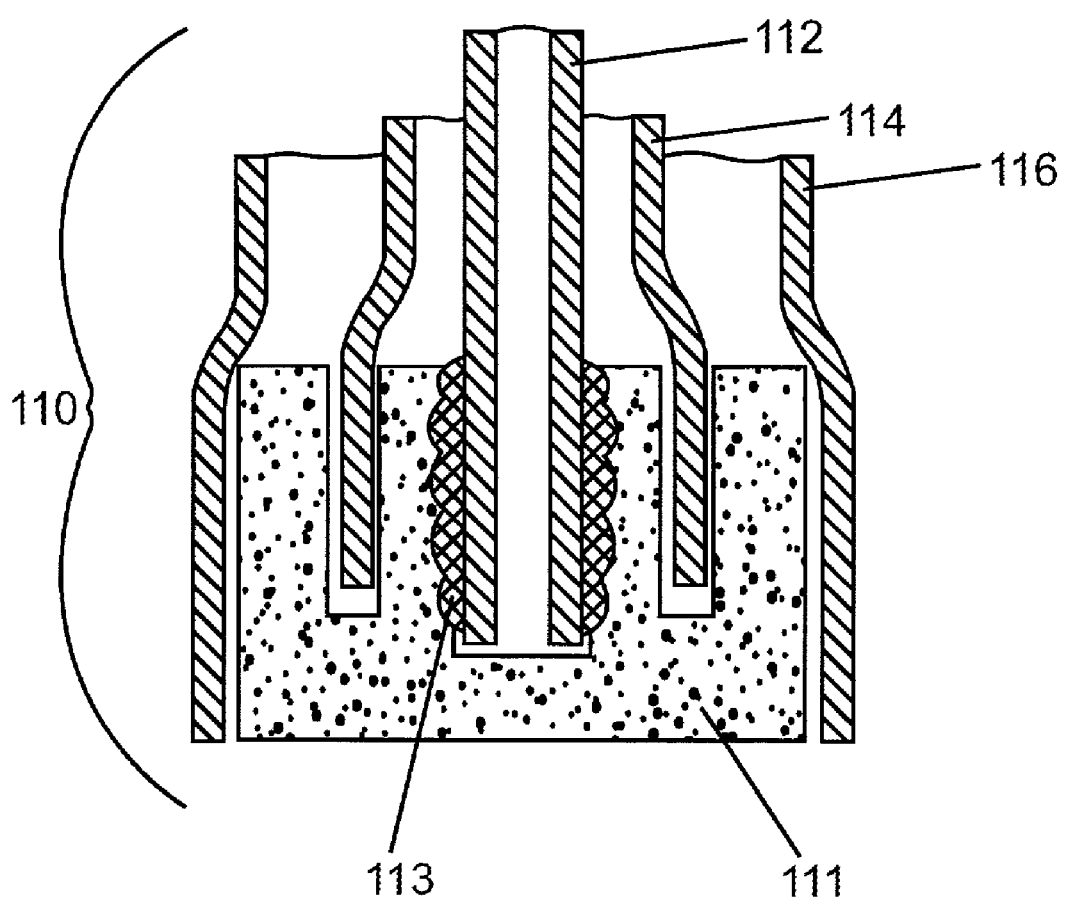
FIG. 11 provides a view of a fluid delivery device according to a fifth embodiment of the subject invention.

Representative views of a fifth representative embodiment are provided in FIG. 11. FIG. 11 provides a cross-sectional view of the distal tip 110 of a delivery device in which all three of the fluid flow lumens, i.e., the first and second fluid introduction lumens and the aspiration lumen, are covered by a porous material though which fluid must flow when entering or leaving the lumens. As shown in FIG. 11, distal tip 110 includes the distal end of first fluid introduction lumen or tube 112, which is concentrically positioned along the central axis of aspiration lumen or tube 114, which in turn is coaxially positioned along the central axis of second fluid delivery lumen or tube 116. Positioned over the openings of all three lumens is porous material 111, which is bonded to the end of the first fluid delivery lumen 112 by adhesive 113.

Sixth Representative Embodiment

Figure 12:
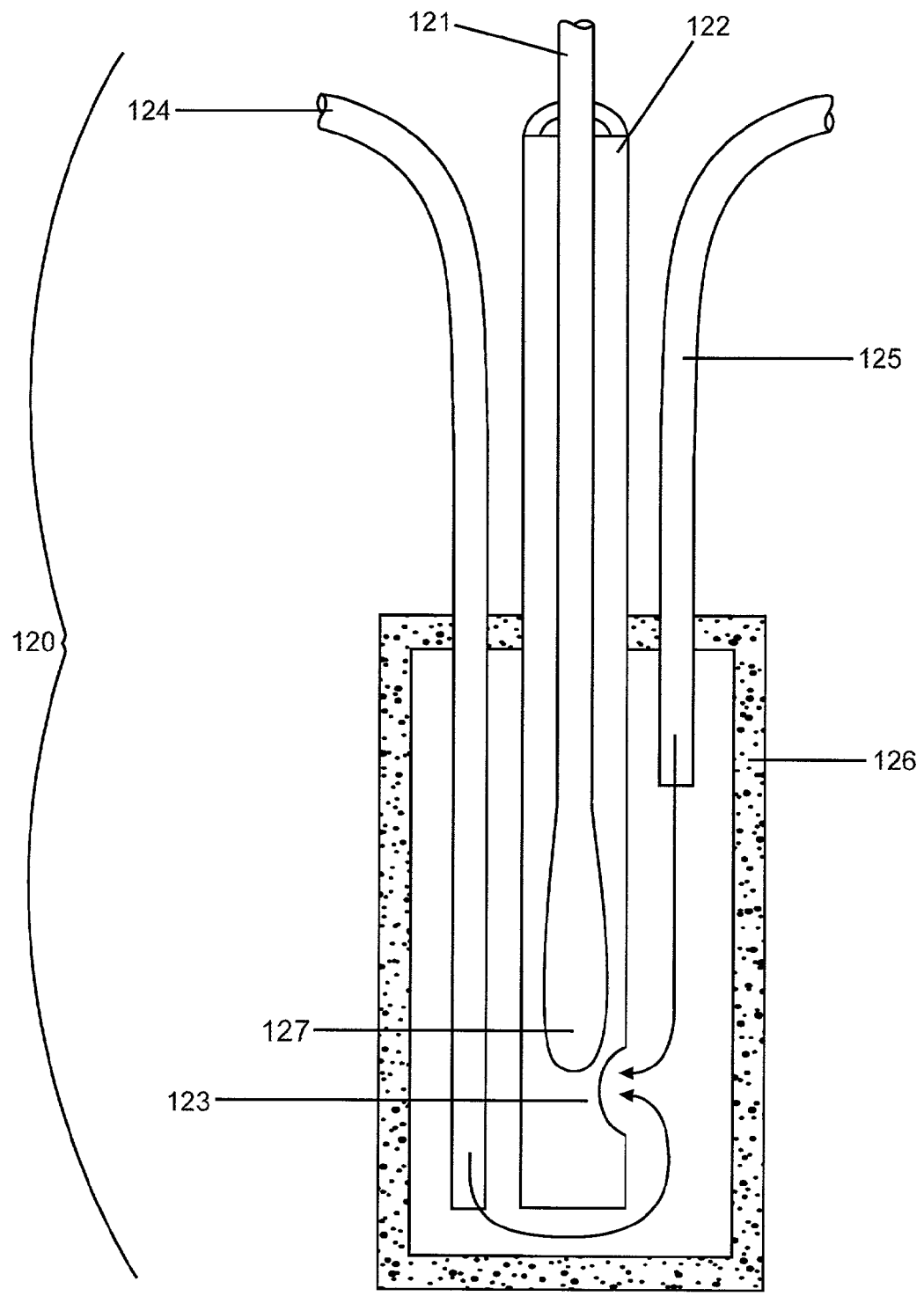
FIG. 12 provides a view of a fluid delivery device according to a sixth embodiment of the subject invention.

Representative views of a sixth representative embodiment of a device having a spatula shaped distal end are provided in FIG. 12. FIG. 12 provides a cross-sectional view of the distal tip 120 of a delivery device in which the distal tip is configured in the form of a spatula for introducing and removing fluid from specific, corresponding target sites. As shown in FIG. 12, the aspiration lumen 122 is a tube into which is positioned a non-compliant guidewire or analogous structure 121 having a wire loop 127 at its distal end. Located on one side of the aspiration lumen 122 adjacent to the distal end is an opening 123 through which fluid flows into the aspiration lumen. Positioned along one outer surface of aspiration lumen 122 is first fluid delivery lumen 124. Positioned opposite from the first fluid delivery lumen 124 is second fluid delivery lumen 125. All three fluid flow lumens are encased in a porous "bag" or analogous encasing structure 126 that provides for controlled delivery of fluid from the various fluid delivery lumens.

Methods

Also provided by the subject invention are methods of locally introducing a fluid, such as an active agent fluid, an organic and/or inorganic matter dissolution solution, etc., to an internal body target site, such as internal vascular site. More specifically, methods are provided for locally administering a fluid to and removing fluid from an internal target site. In other words, methods of locally contacting a target site in a highly localized manner with a fluid are provided.

A feature of the subject methods is that the zone or region to which the fluid is administered is controlled and limited, generally to an area that only slightly exceeds the area that is contacted directly with the porous applicator (tip) or end of the device. As such, the area of tissue which comes in contact with the delivered fluid typically does not exceed the area that is contacted by the porous applicator or end by more than about 50%, usually not more than about 40% and more usually not more than about 25%. In this manner, the delivery of the fluid is carefully limited to a narrow, defined, localized region, i.e., the target site.

Another feature of the subject methods is that the target site is "flushed" with the fluid to be delivered, such that fresh fluid is substantially continuously contacted with the target site, while "old" fluid is removed from the target site.

In practicing the subject methods, the distal end of the delivery device having the region of porosity, i.e., the porous applicator, is first positioned or placed at or near the target site, e.g., it is contacted with the target site, placed adjacent to the target site (where adjacent means no more than about 1.0 mm, usually no more than about 0.5 mm from the target site in many embodiments) etc. Next, fluid is introduced to or contacted with the target site by moving it, e.g., under pressure, along the first fluid delivery lumen and out through the region of porosity, i.e., porous applicator, and the distal end. Depending on the configuration, fluid is flowed through the applicator according to one of the two embodiments shown in FIGS. 1A and 1B, as discussed in greater detail below. Concomitantly, fluid is removed from the target site along the aspiration element. In certain embodiments, the above steps of fluid delivery and removal are accompanied by introduction of a second fluid from a second fluid delivery lumen.

The area of the target site that is contacted with the delivered fluid, e.g., the size of the region that is contacted with the delivered fluid, is influenced, at least to some extent, by the flow rate of the fluid flowing through the fluid delivery lumen and the aspiration rate of fluid from the target site. In certain embodiments, the flow rate of fluid through the first lumen ranges from about 0.5 µl/s to 5 ml/s, usually from about 1.0 µl/s to 1 ml/s and more usually from about 1.0 µl/s to about 0.5 ml/s.

In the broadest sense, the subject delivery devices may be employed to introduce any active agent in a fluid delivery vehicle to a target site using the above general protocols. The subject systems achieve local delivery of active agents in fluid delivery vehicles by contacting the target site with the fluid agent composition. Active agents of interest that may be locally introduced using the subject methods include: thrombolytic agents, growth factors, cytokines, nucleic acids (e.g. gene therapy agents), and the like.

The subject fluid delivery devices find use in any of the fluid delivery protocols described in U.S. Pat. No. 6,156,350 as well as U.S. patent application Ser. Nos. 09/118,193; 09/195,291; 09/353,127; 09/382,571; 09/384,860; 09/425,826; 09/454,235; 09/483,634; 09/528,576; 09/648,282 09/753,023; and 09/774,469; the disclosures of which are herein incorporated by reference.

For purposes of further illustration, a representative method of using the device shown in FIGS. 2 to 6 to remove lesions from the surfaces of aortic valve leaflets is now described.

In these representative methods, the aortic valve leaflets are flushed with a dissolution fluid, where the dissolution fluid may be an organic matter dissolution fluid or an inorganic matter dissolution fluid, or a fluid that is capable of both inorganic matter and organic matter dissolution. Representative dissolution fluids are described in copending U.S. patent application Ser. No. 09/774,469; the disclosure of which is herein incorporated by reference.

In many embodiments, the dissolution fluid employed in the subject methods is an inorganic matter dissolution solution. In many of these embodiments, the inorganic matter dissolution fluid is an acidic dissolution fluid. A variety of different types of acidic dissolution solutions may be employed in the subject methods. The acidic treatment solutions that find use in the subject methods generally have a pH of less than about 6.5, where the pH is usually less than about 4.0 and more usually less than about 3.0. In many preferred embodiments, the pH ranges from 0 to 2, and usually 0 to 1. The acidic treatment solution can include a number of different types of acids, where the acids may or may not include a hydrocarbon moiety, i.e., a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of whole blood, i.e. the osomolarity is greater than 300 mosmol. The solution may be rendered hypertonic by including any convenient component or components in the solution that provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of a hydrogen chloride solution. In hydrogen chloride solutions that find use in the subject invention, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

In certain embodiments, one or more of the delivery fluids is present at a temperature that is less than room temperature. For example, in certain embodiments, the one or more treatment solutions, as described above, is present at a temperature ranging from about 0 to about 20° C., sometimes from about 0 to 15° C., e.g., from about 0 to 10° C. Such embodiments include applications where it is desired to limit restinosis by employing reduced temperature, e.g., cold, solutions.

In practicing the subject methods, the first step is to prepare the host or patient for the procedure. In many embodiments, the host is prepared by placing the host on cardio pulmonary bypass followed by arrest of the heart, e.g., via introduction of a cardoplegia solution to the heart. These procedures are well known to those of skill in the art in the field of cardiology, particular coronary artery bypass graft (CABG) surgery. See e.g., U.S. Pat. No. 6,190,357; the disclosure of which is herein incorporated by reference.

Following preparation of the host/patient/subject, the device shown in FIGS. 2 to 6 is placed in position such that, upon deployment, the target aortic valve surface is isolated from the remainder of the vasculature with the device. In this step, access is first provided to the ascending aorta so that the requisite aortotomy used to introduce the distal end of the device into the aortic root can be cut. Access can be provided using any convenient protocol, including via open chest, an opening produced through the appropriate ribs, etc. Once access is provided, the aortotomy is produced. The aortotomy is produced in the wall of the ascending aorta a point upstream from the brachiocephalic trunk. The length of cut made in the aortic wall may vary depending on the dimensions of the device being employed, but typically ranges in many embodiments from about 0.1 to about 3", usually from about 0.5 to about 2" and more usually from about 0.75 to about 1.5".

Following production of the aortotomy, the device is inserted through the opening into the lumen of the aortic root/ascending aorta. The inserted device is advanced in a retrograde fashion such the distal end of the device extends through the aortic valve into the left ventricle. Following proper positioning of the distal end of the device into the left ventricle, the occlusion element 29 of the device is then moved in an antegrade fashion until the occlusion element is flush with the ventricular side of the aortic valve. Next, the fluid contact elements are moved into the aortic sinuses such that the porous applicator of each contact element is flush with the leaflet surface of each sinus. Where desired, the coronary ostia may be blocked using any convenient protocol, such as with an inflatable balloon etc, where the protocol/device employed may or may not include a blood shunt to provide for blood flow into the coronary arteries during use of the device. Next, the cap structure is compressed against the proximal surface of the fluid contact elements in order to securely hold the fluid contact elements in the aortic sinuses against the valve leaflets.

The aortic valve is then contacted with the dissolution fluid. As the isolated valve is flushed with the dissolution fluid, it is dynamically contacted with the dissolution fluid. By "dynamically contact" is meant that the fresh dissolution solution is contacted with the surface of valve one or more times, including continuously, during the treatment period. In many preferred embodiments of the subject methods, the surface of the valve is continuously contacted or flushed with the acidic dissolution fluid. In other words, the acidic dissolution fluid is introduced in a manner such that a continuous flow of the acidic dissolution fluid across the surface of the valve is achieved. While both the ventricular and aortic surfaces of the valve may be contacted with the dissolution fluid, in many embodiments the aortic surface and commissurs are contacted with the dissolution fluid, with substantially less fluid contact of the ventricular surface of the valve, if any.

In certain embodiments, it is desirable to employ a dissolution fluid attenuating fluid so as to ensure that only the aortic surface of the artic valve, and not the remainder of the tissue present in the local environment, e.g., aortic root, left ventricle etc., is contacted with a low pH solution. Such embodiments ensure that the remainder of the isolated local environment or vascular site is contacted with a fluid that has a pH well above that of the acidic dissolution fluid, where the lowest pH to which the remainder of the target vascular site is subjected is not less than 4, preferably not less than 5 and more preferably not less than 6. In other words, only the aortic surface of the target valve is contacted with the low pH acid dissolution fluid while the remainder of the target vascular site, e.g., the ventricular side, the coronary ostia, the intimal surface of the aortic sinuses, etc., is contacted with a solution the pH of which is not less than 4, preferably not less than 5 and more preferable not less than 6.

The nature of the dissolution solution attenuating fluid necessarily depends on the nature of the dissolution fluid, where representative pairs of fluids and their attenuating counterparts are described in U.S. patent application Ser. No. 09/774,469, the disclosure of which is herein incorporated by reference.

Where the dissolution fluid is an acidic dissolution fluid, attenuating fluids of particular interest are pH elevating fluids. By pH elevating solution is meant any solution that, upon combination with the acidic dissolution solution, produces a solution with an elevated pH with respect to the acidic dissolution solution. In principle, any fluid that, upon combination of with the acid dissolution fluid produces a solution having a pH higher than that of the acidic dissolution fluid, may be employed, so long as the fluid is biocompatible, at least for the period of time that it is present in the target vascular site. The pH elevating solution should have a pH of at least about 4, usually at least about 6 and more usually at least about 8. As such, pH elevating fluids of interest include water, physiological acceptable buffer solutions, etc., where in many embodiments, the pH elevating solution is a buffer solution. Representative buffer solutions of interest include: phosphate buffered saline, sodium bicarbonate and the like.

When employed, the dissolution fluid attenuating solution, e.g., buffer, may be employed in a variety of different ways, e.g., introduced into the aorta upstream of the contact site so as to ensure that any escaping acid is neutralized.

The isolated aortic valve is contacted with at least the dissolution fluid for a period of time sufficient to achieve the desired result. The desired result necessarily depends on the application being performed, where representative desired results are described below in the section entitled "Utility." While the period of time that the valve is flushed may vary, the period of time typically ranges from about 1 minute to about 4 hrs, usually from about 15 minutes to about 1 hour and more usually from about 20 minutes to about 45 minutes.

In certain embodiments, the method includes subjecting to the porous applicator of the fluid contact element to compressive force, typically in an interative or pulsatile fashion, which results in fluid present in the applicator being forced or driven out of the applicator and into the target site.

Following contact or flushing for the desired period of time, the device is then removed from the patient. The device may be removed using any convenient protocol. In one representative protocol, the occlusion balloons are deflated and then the device is removed from the ascending aorta through the aortotomy. The patient may then be removed from heart/lung bypass and the heart may be started using conventional procedures, followed by surgical closing and postoperative care standard to those of skill in the art.

While the above representative embodiment was described in terms of a open surgical, stopped heart application, one of skill in the art will appreciate that an analogous protocol on a beating heart with a catheter based device according to the subject invention is also provided within the scope of the present application.

Optional Method Steps

In a number of embodiments of the subject methods, the above described methods may be modified to include a number of additional method steps. Additional method steps that may be present in the overall process include: rendering the local environment of the isolated aortic valve bloodless, washing or rinsing the isolated local environment of the aortic valve, applying external energy to the aortic valve during treatment; imaging the isolated vascular site; and the like.

Rendering the Local Environment Bloodless

In certain embodiments, as described above, the local environment of the aortic valve is rendered substantially bloodless prior to introduction of the acidic dissolution fluid. In these embodiments, the isolation system is deployed to physically isolate the local environment from the remainder of the circulatory system and then the local environment is flushed with a physiologically acceptable solution, such that substantially all of the blood present in the solution is removed. Typically, a washing solution will be employed in this step of rendering the local environment bloodless. Examples of washing solutions that may find use in these embodiments include: water for injection, saline solutions, e.g. Ringer's, phosphate buffered saline, or other physiologically acceptable solutions. The washing solution may include an anticlotting factor in many embodiments, where anticlotting factors of interest include heparin and the like. The washing solution can also contain chelating agents.

Application of External Energy

In certain embodiments, external energy is applied to the target aortic valve to promote mechanical break-up of the calcified deposits into particles or debris that can be easily removed from the vascular site. Any means of applying external energy to the aortic valve may be employed. As such, jets or other such means the device which are capable of providing varying external forces to the target deposits cause the target deposit to break up or disrupt may be employed. Of particular interest in many embodiments is the use of sonic energy, e.g., ultrasound. Another means that may be employed to apply external energy to the lesion during the dissolution process is to use a mechanical means of applying external energy. Mechanical means of interest include moving structures, e.g. rotating wires, guidewires, which physically contact the target lesion and thereby apply physical external energy to the target lesion.

Imaging

In addition, it may be convenient to monitor or visualize the vascular site prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital subtraction fluoroscopy, cinefluorography, conventional, helical and electron beam computed tomography, intravascular ultrasound (IVUS), magnetic resonance imaging, transthoracic and transesophageal echocardiography, rapid CT scanning, antioscopy and the like. Any of these means can be used to monitor the vascular site before, during or after contact with the dissolution fluid.

In many embodiments, an imaging agent is employed, where the imaging agent may or may not be present in the acidic dissolution solution. Imaging agents of particular interest include: non-ionic imaging agents, e.g. CONRAY™, OXILAN™, and the like.

Systems

Also provided by the subject invention are systems for practicing the subject methods, i.e., for enhancing fluid flow through a vascular site occupied by a vascular occlusion. The subject systems at least include a fluid delivery device of the present invention, as described above, a manifold, a fluid reservoir for storing dissolution fluid, a fluid reservoir for storing a dissolution fluid attenuating fluid (when employed) and a vacuum or analogous aspiration force generating element for providing aspiration or suction during use of the system. The systems may further include a number of optional components, e.g. guidewires, pumps for pressurizing the dissolution fluid, and the like. See e.g. U.S. patent application Ser. No. 09/384,860, the disclosure of which is herein incorporated by reference.

Utility

The subject devices and methods find use in a variety of different applications in which it is desired to deliver fluid to a target site in a localized manner. As such the subject methods and devices may be employed to administer a fluid to an internal target site, to deliver a fluid to an external target site, to deliver fluid to a surgically accessible target site, etc.

With respect to the above described representative methods and devices related to FIGS. 2 to 7, these representative methods and devices find use in any application in which it is desired to contact an isolated aortic valve with a fluid, e.g., a fluid composition of a therapeutic agent. The subject devices and methods are particularly suited for use in the treatment of aortic stenosis. The term "aortic stenosis" is used broadly to refer to any condition that is characterized by disease and narrowing of the valve such that fluid flow through the valve is impeded. In many instances, the target aortic stenosis condition of the subject methods is characterized by having calcification present on the valve leaflets that reduces or impedes mobility of the leaflets. Of particular interest is the treatment of aortic stenosis characterized by calcified deposits on the leaflet surface in which the calcification results in a aortic valve flow (as measured by the cardiac catheterization technique known in the art as the gold standard for evaluating aortic stenosis) that is less then 3.0, often less than about 2.5 and more often less than about 2.0, where in many embodiments the aortic valve flow may be less than 1.0.

Treatment of aortic stenosis according to the subject invention results in at least a reduction in the amount of calcium phosphate mineral present on a stenotic valve surface, i.e., the aortic side leaflet surface. The amount of reduction that is achieved with the subject invention is typically at least about 10%, usually at least about 20% and more usually at least about 30% by weight.

In many embodiments, treatment according to the subject methods results in an increase in aortic valve flow, as determined using the cardiac catheterization protocol described above. The amount of increase that is achieve is generally at least about 0.5 units, usually at least about 1.0 unit. In many embodiments, the aortic valve flow is improved to a value that is at least about 1, preferably at least about 1.5 and more preferably at least about 2.0, where one may achieve even higher values, including the normal 3.0, in certain embodiments.

Treatment also typically results in amelioration of one or more symptoms associated with, e.g., caused by, aortic stenosis, including but not limited to: chest pain, fainting, shortness of breath, delayed upstroke and lower intensity of the carotid pulse, heart murmur, abnormal EKG patterns, etc.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

Kits

Also provided by the subject invention are kits for use in practicing the subject methods. The subject kits at least include a fluid delivery device of the subject invention, as described above. The fluid delivery device may be present as an integral unit, or in one more components that need to be put together during use. For example, the fluid contact elements may be presented separate from the remainder of the device in the kit, and a plurality of different sizes of contact elements may be provided to allow a tailored fit to be produced during use. The kits may further include one or more additional components and accessories for use with the subject fluid delivery devices, including tubing for connecting the various catheter components with fluid reservoirs, syringes, pumping means, etc., connectors, one or more guidewires, dilators, vacuum regulators, etc.

In certain embodiments, the kits further include one or more solutions, or precursors thereof (e.g., dried reagents for combination with water or another solvent), where in such embodiments the kits at least include an acidic dissolution fluid, such as a hydrochloric acid solution, as described above, where the solution may be present in a container(s), e.g. a flexible bag, a rigid bottle, etc. For kits that are to be used in methodologies in which the fluid is flushed through the local environment of the lesion, the amount of dissolution fluid present in the kit ranges from about 0.5 to 500 liters, usually from about 0.5 to 200 liters and more usually from about 0.5 to 100 liters. In many embodiments, the amount of dissolution fluid in the kit ranges from 0.5 to 5 liters, usually from about 0.5 to 2.0 liters and more usually from about 0.5 to 1.5 liters. Alternatively, the kit may comprise precursors or components of the dissolution solution for use in preparing the solution at the time of use. For example, the precursors may be provided in dry form for mixing with a fluid, e.g. water, at the time of use. In addition to the dissolution fluid or precursors thereof, the kit may further comprise one or more additional fluids (or dry precursors thereof), such as a priming solution, a washing solution, contrast medium, and the like. In many embodiments, the kits further include at least a pH elevating solution, e.g., a buffer solution such as phosphate buffered saline.

Other elements that may be present in the subject kits include various components of the systems, including manifolds, balloon inflation means, e.g. syringes, pumping means, negative pressure means etc.

In addition to above mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following example is offered by way of illustration, and not by way of limitation.

EXPERIMENTAL

I. The following protocol is representative of the methods according to the subject invention, where the device employed is that depicted in FIGS. 7A and 7B.

A. Treatment Site Access
 1. Create exposure and initiate cardiac arrest.
 2. Access the treatment site through a standard transverse aortotomy used for aortic valve replacement.

B. Treatment Procedure
 1. Place a coronary occlusion element in each coronary ostium.
 2. Insert the tip of the applicator catheter through the aortic valve until the balloon is just below the annulus of the valve.
 3. Ensure that the catheter is centrally located and generally perpendicular to the plane of the aortic valve.

4. Inflate the occlusion balloon and the slave balloon until gentle tension on the catheter fails to raise the proximal balloon surface above the level of the valve commisures.
5. Apply gentle tension to the shaft of the catheter to seat the distal balloon against the aortic valve leaflets.
6. Inject approximately 5 cc of saline into the aortic root and verify that the fluid level remains constant for at least 15 seconds. If fluid drains from the root, inflate the balloon using an additional 2 cc of saline. Ensure that tension is still properly applied to the catheter and repeat the fluid leak test until the fluid level remains constant for at least 15 seconds.
7. Compress a foam applicator element (fluid contact element) in a pair of forceps and place it over one of the aortic valve leaflets. Repeat until all three foam elements have been properly seated in the cusps of the aortic valve leaflets.
8. Slide the locking cap down the catheter shaft and compress the foam elements while applying tension to the applicator catheter until the black line appears just above the locking cap.
9. Initiate aspiration.
10. Open the pinch clamps on the tubing set.
11. Initiate CDS (HCl dissolution fluid) and buffer flow.
12. Confirm that CDS and buffer are flowing by observing the drip chambers.
13. Confirm that the aspiration is working by looking for fluid in the aspiration line.
14. Confirm that fluid is not leaking around the locking cap.
15. Allow the treatment to procede for a period of 30 minutes.
16. After 30 minutes, stop the flow of CDS and buffer and turn off the aspiration.
17. Slide the locking cap back up the catheter shaft.
18. Remove each of the foam application elements.
19. Flush the treatment area with saline and aspirate.
20. Deflate the balloons and remove the catheter.
21. Remove the catheter occlusion elements.
22. Flush and aspirate the treatment area as needed.
23. Close the aortotomy site.
24. Continue the procedure with anastomosis and de-airing as needed.

It is evident from the above discussion and results that improved devices and methods of locally delivering a fluid to an internal target site are provided. Specifically, the subject devices and methods provide for highly localized administration of an active agent to an internal target site, such as a target vascular site. The methods and devices provide a number of advantages over existing technologies, including reduced complications due to systemic contact of administered active agents, ability to provide for highly localized delivery in a percutaneous manner, and the like. As such, the subject invention represents a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device for locally contacting aortic valve leaflets with a demineralization fluid, the device comprising:
    a central shaft;
    three distinct fluid contact elements arranged around the central shaft, each fluid contacting element comprising a porous applicator affixed to an impermeable backing, wherein the impermeable backing is located only at proximal end of the porous applicator; the distal ends of the fluid contacting elements being configured to fit snugly inside of the aortic sinus;
    fluid delivery elements for delivering a demineralization fluid from a source to the porous applicators;
    a shunt positioned within the central shaft and concentrically mounted therein for providing blood flow from the ventricle;
    an aspiration lumen formed from a gap between the shunt and the central shaft; and
    a valve occluder mounted to the central shaft, the valve occluder being configured to sit flush with the ventricular side of the aortic valve leaflets.

* * * * *